(12) United States Patent
Harada et al.

(10) Patent No.: US 7,750,298 B2
(45) Date of Patent: Jul. 6, 2010

(54) INTERFEROMETER HAVING THREE ELECTRON BIPRISMS

(75) Inventors: Ken Harada, Wako (JP); Tetsuya Akashi, Fujimi (JP); Yoshihiko Togawa, Wako (JP); Tsuyoshi Matsuda, Wako (JP); Noboru Moriya, Wako (JP)

(73) Assignee: Riken, Saitama (JP)

( * ) Notice: Subject to any disclaimer, the term of this patent is extended or adjusted under 35 U.S.C. 154(b) by 173 days.

(21) Appl. No.: 11/884,680

(22) PCT Filed: Jan. 27, 2006

(86) PCT No.: PCT/JP2006/301334

§ 371 (c)(1),
(2), (4) Date: Aug. 20, 2007

(87) PCT Pub. No.: WO2006/090556

PCT Pub. Date: Aug. 31, 2006

(65) Prior Publication Data

US 2008/0258058 A1    Oct. 23, 2008

(30) Foreign Application Priority Data

Feb. 23, 2005   (JP)   ............................. 2005-046633

(51) Int. Cl.
*G21G 5/00*    (2006.01)
(52) U.S. Cl. ................. 250/311; 250/492.1; 250/492.2; 250/492.3; 250/306; 250/307; 250/310
(58) Field of Classification Search ............. 250/492.1, 250/492.2, 492.3, 306, 307, 310, 311
See application file for complete search history.

(56) References Cited

U.S. PATENT DOCUMENTS

| | | | |
|---|---|---|---|
| 6,759,656 B2 | 7/2004 | Tomita | |
| 6,950,195 B2 | 9/2005 | Endo et al. | |
| 7,538,323 B2 * | 5/2009 | Harada et al. | 250/310 |
| 2008/0302965 A1 * | 12/2008 | Harada et al. | 250/311 |

FOREIGN PATENT DOCUMENTS

| | | |
|---|---|---|
| JP | 08-153485 | 6/1996 |
| JP | 08-153485 | 11/1996 |
| JP | 2002-117800 | 4/2002 |
| JP | 2005-197165 | 7/2005 |
| WO | 01/75394 | 10/2001 |

OTHER PUBLICATIONS

International Search Report mailed May 16, 2007 (English and Japanese Text).
Harada et al.: "Double-biprism electron interferometry," Applied Physics Letters, vol. 84, No. 17, Apr. 26, 2004, pp. 3229-3231.
Harada et al., "Double-biprism electron interferometry", Applied Physics Letters, American Institute of Physics, Apr. 26, 2004, vol. 84, No. 17, pp. 3229-3231.

* cited by examiner

*Primary Examiner*—Jack I Berman
*Assistant Examiner*—Hanway Chang
(74) *Attorney, Agent, or Firm*—Nixon & Vanderhye PC

(57) ABSTRACT

An interferometer is disclosed which has upper-stage, intermediate-stage, and lower-stage electron biprisms. The disclosed interferometer operates with an azimuth angle $\Phi$ among filament electrodes of the three electron biprisms to arbitrarily control an interference area and an azimuth $\theta$ of the interference fringes formed therein, eliminates Fresnel fringes generation, and allows independent control of an interference fringe spacing s and the azimuth $\theta$ of the interference fringes.

10 Claims, 15 Drawing Sheets

$\phi_1 = 50°$
$\phi_3 = 45°$ $\phi_1 = 70°$
$\phi_3 = 45°$ $\phi_1 = 90°$
$\phi_3 = 45°$ $\phi_1 = 110°$
$\phi_3 = 45°$ $\phi_1 = 90°$
$\phi_3 = 30°$ $\phi_1 = 90°$
$\phi_3 = 45°$ $\phi_1 = 90°$
$\phi_3 = 60°$ $\phi_1 = 90°$
$\phi_3 = 30°$
$V_3 = 0V$ $\phi_1 = 90°$
$\phi_3 = 30°$
$V_3 = 40V$ $\phi_1 = 90°$
$\phi_3 = 30°$
$V_3 = 90V$ $\phi_1 = 90°$
$\phi_3 = 30°$
$V_3 = 140V$ 100nm 100nm

INTERFEROMETER HAVING THREE ELECTRON BIPRISMS

This application is the U.S. national phase of International Application No. PCT/JP2006/301334 filed 27 Jan. 2006 which designated the U.S. and claims priority to JP 2005-046633 filed 23 Feb. 2005, the entire contents of each of which are hereby incorporated by reference.

TECHNICAL FIELD

The present invention relates to an interferometer using a charged particle beam such as an electron or ion, or an interferometer using light, and using three biprisms.

BACKGROUND ART

The present inventors have developed and introduced a double-biprism electron interferometer (Japanese Patent Applications Nos. 2004-004156 and 2004-102530, and Non-Patent Documents 1 and 2). In the invention, two electron biprisms are arranged in order of the traveling direction of an electron beam on an optical axis in such a manner that the upper-stage biprism is located on an image plane of a specimen observed and that the lower-stage biprism is located in the shadow area of the upper-stage biprism and voltages applied to their respective filament electrodes of the electron biprisms are changed so that an overlap area (corresponding to an interference area width W) and an overlap angle (corresponding to an interference fringe spacing s) of two electron waves (e.g., an object wave and a reference wave) can be changed arbitrarily. The upper-stage electron biprism is located on the image plane of the specimen, making it possible to eliminate generation of Fresnel fringes superimposed on an interference area, such as a hologram, which cannot be eliminated, in principle, in an electron interferometer using one electron biprism (for instance, Patent Document 1).

In addition to this, the present inventors have proposed an invention in which an azimuth angle $\Phi$ is introduced between filament electrodes of two electron biprisms to control an azimuth $\theta$ of the interference fringes (Japanese Patent Application No. 2005-027274).

There is an interferometer using a charged particle beam such as an electron or ion or an optical interferometer using light beam. In the present invention, the interferometer using an electron beam will be mainly described.

Patent Document 1: Japanese Patent Application Laid-Open Publication No. 2002-117800

Non-Patent Document 1: "Double-Biprism Electron Interferometry", Ken Harada, Tetsuya Akashi, Yoshihiko Togawa, Tsuyoshi Matsuda and Akira Tonomura, Applied Physics Letter: Vol. 84, No. 17, (2004) pp. 3229-3231.

Non-Patent Document 2: "High-Resolution Observation by Double-Biprism Electron Holography", Ken Harada, Tsuyoshi Matsuda, Tetsuya Akashi, Yoshihiko Togawa and Akira Tonomura, Journal of Applied Physics: Vol. 96, No. 9, (2004) pp. 6097-6102.

DISCLOSURE OF THE INVENTION

Problems to be Solved by the Invention

The double-biprism electron interferometer and the modified double-biprism electron interferometer in which the azimuth angle $\Phi$ is introduced between filament electrodes of two electron biprisms, according to the present inventors, dramatically increase the degree of freedom of a conventional one-stage electron biprism interferometer and can control the azimuth $\theta$ of the interference fringes of an electron hologram. A specimen in a shape extended in one direction such as a carbon nanotube can be easily observed in the longitudinal direction of the specimen.

In the invention of Japanese Patent Application No. 2005-027274, the relation between the interference fringe spacing s and the azimuth $\theta$ of the interference fringes is in a simple form, as described in Equation (10) of Japanese Patent Application No. 2005-027274 and cannot be controlled independently. With introduction of the azimuth angle $\Phi$ between filament electrodes of two electron biprisms, the filament electrode of the lower-stage electron biprism extends off the shadow area of the filament electrode of the upper-stage electron biprism. Accordingly, slight superimposition of Fresnel fringes on an interference area is caused.

There is desired an interferometer which can perform independent control of three parameters of the interference area width W, the interference fringe spacing s, and the azimuth $\theta$ of the interference fringes by an easy operation.

Means for Solving the Problems

The present invention realizes the above problems using three electron biprisms simultaneously. Filament electrodes of the upper and intermediate electron biprisms are located on respective image planes of a specimen. The azimuth angle $\Phi_1$ is given between the electrodes. The relative positions of four real sources caused by allowing both the electron biprisms to function are operated in an XY plane which is orthogonal to the optical axis, by applying voltages to the filament electrodes. The interference fringe spacing s and the azimuth $\theta$ of the interference fringes can be controlled arbitrarily. The azimuth angle $\Phi_3$ is given to the filament electrode of the lowermost-stage electron biprism, making it possible to provide arbitrary interference area widths ($W_x$ and $W_y$) in the X and Y directions.

The three electron biprisms are used to provide a parallelogram-shaped interference area of arbitrary shape and size to arbitrarily control the interference fringe spacing s and the azimuth $\theta$ of the interference fringes formed therein.

EFFECT OF THE INVENTION

According to the present invention, in addition to the interference area width W, the interference fringe spacing s, and the azimuth $\theta$ which can be controlled in the invention of Japanese Patent Application No. 2005-027274, the interference fringe spacing s and the azimuth $\theta$ can be controlled independently and the shape of the interference area can be controlled as the parameters of the arbitrary interference area widths ($W_x$ and $W_y$). A new degree of freedom is provided to treating of electron interferometry. Adjustment of the interference fringe spacing s and the azimuth $\theta$ of an interferogram, which has been performed only by the procedure of image reconstruction in the conventional electron holography, can be directly done by an electron beam in an electron microscope. Direct observation and recording of the interferogram can be done in an electron optical system under arbitrary interference conditions without image processing after recording, such as hologram reconstruction. The operability and performance of a wavefront-splitting type interferometer are comparable to those of an amplitude-splitting type interferometer.

The Fresnel fringes superimposed on the hologram which cannot be eliminated the invention of Japanese Patent Application No. 2005-027274 can be eliminated.

BEST MODE FOR CARRYING OUT THE INVENTION

The present invention uses three electron biprisms, and operates the azimuth angle $\Phi_1$ between filament electrodes of upper-stage and intermediate-stage electron biprisms to arbitrarily control an interference area and the azimuth $\theta$ of the interference fringes formed therein. In addition to this, the azimuth angle $\Phi_3$ is given to an filament electrode of the lower-stage electron biprism, making it possible to provide the arbitrary interference area widths ($W_x$ and $W_y$) in the X and Y directions. As a result, an arbitrary interference area of a parallelogram shape can be provided.

An interferometer so called modified double-biprism electron interferometer having upper-stage and lower-stage electron biprisms and operation with the azimuth angle $\Phi$ between the filament electrodes of the upper-stage and lower-stage electron biprisms as a basis of the present invention will be described.

FIG. 1 is a diagram showing an interference optical system using the electron biprisms explained in FIG. 3 of Japanese Patent Application No. 2004-004156.

In FIG. 1, the reference numeral 1 denotes an electron source, the reference numeral 2 denotes an optical axis, the reference numeral 3 denotes a specimen, the reference numeral 5 denotes an objective lens system having one or more lenses (In the drawing, for simplification, one equivalent lens is represented. A distance $a_1$ from the lens to the electron source and a distance $b_1$ from the lens to an image plane of an electron source are distances corresponding to the same and are different from the actual size of the apparatus. This is ditto for the drawings after FIG. 1.), the reference numeral 7 denotes a first image plane of an electron source just above the upper-stage electron biprism, the reference numeral 11 denotes an observation plane, the reference numeral 12 denotes a specimen image on the observation plane, and the reference numeral 13 denotes image recording means such as a film or camera. The reference numerals 21 and 23 respectively denote an object wave and a reference wave. The reference numeral 31 denotes a specimen-image plane by the objective lens system 5, the reference numeral 32 denotes a specimen image by the objective lens system 5, the reference numeral 33 denotes a magnifying lens, the reference numeral 35 denotes an image plane of an electron source by the magnifying lens 33, and the reference numeral $9_u$ denotes a filament electrode of the upper-stage electron biprism located on the specimen-image plane 31 by the objective lens system and has a diameter $d_u$. The reference numeral $9_b$ denotes a filament electrode of the lower-stage electron biprism located between the image plane of an electron source 35 by the magnifying lens 33 and the observation plane 11 and has a diameter $d_b$. The interference fringe spacing s and the interference area width W appearing on the observation plane 11 are schematically shown under the recording means 13. Here, the electron source 1 is shown in a single block in the drawing, and includes a source, an acceleration tube, and a condenser optical system. The electron biprism of the schematic diagram shown here is of an electric field type, has a filament electrode of an extrafine wire at the center and grounding electrodes on the right and left sides of the outside far the position through which an electron beam passes, and applies a voltage to the filament electrode at the center to deflect the electron beam. In FIG. 1 and the drawings thereafter, the cross section or the end section of the filament electrode at the center is indicated by a small circle. In the description noting the function of the electron biprism, only the electron biprism is represented. In the description noting the filament electrode at the center, the filament electrode of the electron biprism is represented. An electron optical system typically uses a magnetic field type electromagnetic lens as an electron lens, and includes rotation about an axis in parallel with the optical axis in the path of the electron beam. FIG. 1 neglects azimuth rotation of the electron beam by the electromagnetic lens and shows an electron optical system on the same plane. This is ditto for the drawings showing the optical system.

An electron beam emitted from the electron source 1 is split into the object wave 21 passing through the specimen 3 located on one side of the optical axis 2 and the reference wave 23 passing through the side without the specimen 3. To easily identify the object wave 21 and the reference wave 23, only the object wave 21 is patterned. The object wave 21 and the reference wave 23 are refracted by the objective lens system 5 to cross on the image plane of the electron source 7 just above the upper-stage electron biprism for traveling to the magnifying lens 33. The object wave 21 and the reference wave 23 form the specimen image 32 on the image plane of the specimen 31 by the objective lens system 5 and pass through the position of the upper-stage electron biprism on the image plane 31. Both the electron beams of the object wave 21 and the reference wave 23 are deflected toward the optical axis 2 by deflection of an applied voltage $V_u$ to the filament electrode $9_u$ of the upper-stage electron biprism. Two split real images of electron source 26 and 28 are formed on the downstream side of the magnifying lens 33. Both the electron beams of the object wave 21 and the reference wave 23 are deflected by an applied voltage $V_b$ to the filament electrode $9_b$ of the lower-stage electron biprism and form virtual images of electron source 25 and 27. $Y_r$ is a split distance from the optical axis to the real source 26 caused by the deflection by the filament electrode $9_u$ of the upper-stage electron biprism, and $Y_v$ is a split distance from the real image of electron source 26 to the virtual image of electron source by the deflection by the filament electrode $9_b$ of the lower-stage electron biprism. They are expressed as Equations (1) and (2). Here, $a_3$ is a distance between the first image plane of electron source 7 and the magnifying lens 33, $b_3$ is a distance between the magnifying lens 33 and the second image plane of electron source 35, $\alpha_u$ is a deflection angle of the electron beam by the upper-stage electron-biprism electrode $9_u$, $b_{Obj}$ is a distance between the first image plane 31 and the objective lens system 5, $b_1$ is a distance between the objective lens system 5 and the first image plane of electron source 7, $D_u$ is a distance between the first image plane of electron source 7 and the first image plane 31, $\alpha_b$ is a deflection angle of the electron beam by the lower-stage electron-biprism electrode $9_b$, $b_M$ is a distance between the magnifying lens 33 and the observation plane 11, $b_3$ is a distance between the magnifying lens 33 and the second image plane of electron source 35, $L_b$ is a distance between the lower-stage electron-biprism electrode $9_b$ and the observation plane 11, and $D_b$ is a distance between the second image plane of electron source 35 and the observation plane 11.

$$Y_r = \frac{b_3}{a_3} \cdot \alpha_u (b_{Obj} - b_1) = \frac{b_3}{a_3} \cdot a_u D_u \quad \text{[Equation 1]}$$

$$Y_v = \alpha_b (b_M - b_3 - L_b) = \alpha_b (D_b - L_b) \quad \text{[Equation 2]}$$

The observation plane 11 is an image plane of the filament electrode $9_u$ of the upper-stage electron biprism. The deflection function on the upper-stage electron biprism does not influence the image formation and overlap of the wavefront does not occur. A real deflection to the electron beam, however, is performed, the splits 26 and 28 of the real images of the electron source are caused. This is essentially the same as the splits 25 and 27 of the virtual images of the electron source by the filament electrode $9_b$ of the lower-stage electron biprism.

The interference fringes backprojected to the object plane of the objective lens system where the specimen is positioned when both the electron biprisms $9_u$ and $9_b$ simultaneously work in the optical system shown in FIG. 1 are expressed as Equations (3) and (4). $M_{Obj}$ is a magnification by the objective lens system 5 to the specimen 3, and $M_M$ is a magnification by the magnifying lens 33 to the specimen image 32. In FIG. 1 and its explanation, magnification is shown for convenience and arbitrary magnification change including demagnification according to the lens and the use of the lens system is intended. This is ditto for the following explanation. The interference fringe spacing s and the interference area width W of the interference fringes backprojected onto the object plane are expressed by a subscript Obj. Here, $a_M$ is a distance between the magnifying lens 33 and the electron-biprism electrode $9_u$, $a_{Obj}$ is a distance between the specimen 3 and the objective lens system 5, and $\lambda$ is a wavelength of the electron beam emitted from the electron source 1.

$$S_{Obj} = \frac{a_M}{b_M} \cdot \frac{a_{Obj}}{b_{Obj}} \cdot \frac{D_b \lambda}{Y_v + Y_u} \quad \text{[Equation 3]}$$
$$= \frac{a_M}{b_M} \cdot \frac{a_{Obj}}{b_{Obj}} \cdot \frac{a_3(b_M - b_3)\lambda}{2\{\alpha_b a_3(b_M - b_3 - L_b) + \alpha_u b_3(b_{Obj} - b_1)\}}$$
$$= \frac{1}{M_M} \cdot \frac{1}{M_{Obj}} \cdot \frac{a_3 D_b \lambda}{2\{\alpha_b a_3(D_b - L_b) + \alpha_u b_3 D_u\}}$$

$$W_{Obj} = \frac{a_M}{b_M} \cdot \frac{a_{Obj}}{b_{Obj}} \cdot \frac{2Y_v L_b}{D_b - L_b} - \frac{a_{Obj}}{b_{Obj}} d_u \quad \text{[Equation 4]}$$
$$= \frac{a_M}{b_M} \cdot \frac{a_{Obj}}{b_{Obj}} \cdot 2\alpha_b L_b - \frac{a_{Obj}}{b_{Obj}} d_u$$
$$= \frac{1}{M_M} \cdot \frac{1}{M_{Obj}} \cdot 2\alpha_b L_b - \frac{1}{M_{Obj}} d_u$$

Equations (3) and (4) mean that the interference area width $W_{Obj}$ is not dependent on the deflection angle $\alpha_u$ by the upper-stage electron biprism. This allows independently control of the interference fringe spacing $s_{Obj}$ and the interference area width $W_{Obj}$. To be more specific, independent operation can be done by the following procedure:

(1) The lower-stage electron biprism→The interference area width $W_{Obj}$ is determined.
(2) The upper-stage electron biprism→The interference fringe spacing $s_{Obj}$ is adjusted.

One of the optical condition, $(D_b - L_b = 0)$, means that the filament electrode $9_b$ of the lower-stage electron biprism is placed in the position of the image plane of the electron source 35 by the magnifying lens 33. In this case, in Equation (3), the interference fringe spacing $s_{Obj}$ is not dependent on the deflection angle $\alpha_b$ of the lower-stage electron biprism. Under the optical conditions, perfectly independent control of the interference fringe spacing $s_{Obj}$ and the interference area width $W_{Obj}$ can be done with using both the biprisms.

In the invention of Japanese Patent Application No. 2004-004156, the electron interferometer which can independently control the interference fringe spacing $s_{Obj}$ and the interference area width $W_{Obj}$ can be realized. As described in Problems to be Solved by the Invention, the one-dimensional shape of an electron hologram formed by the filament electrodes, the direction of the interference area, and the azimuth θ of the interference fringes are the same as the optical system of the one-stage electron biprism. The longitudinal direction of the interference area is determined corresponding to the direction of the filament electrodes and the azimuth θ of the interference fringes coincides with and is in parallel with the longitudinal direction of the interference area.

In the invention of Japanese Patent Application No. 2005-027274, an interferometer has upper-stage and lower-stage electron biprisms, and operates with the azimuth angle Φ between filament electrodes of the upper-stage and lower-stage electron biprisms to arbitrarily control the interference area and the azimuth θ of the interference fringes formed therein. It will be described specifically.

FIG. 2 is a schematic diagram for explaining formation of interference fringes obtained by an optical system with the azimuth angle Φ between filament electrodes of upper-stage and lower-stage electron biprisms explained in FIG. 2 of Japanese Patent Application No. 2005-027274 and for showing a three-dimensional structure to easily understand the azimuth angle Φ between the filament electrodes of the upper-stage and lower-stage electron biprisms. FIG. 3 is also a schematic diagram of an optical system with the azimuth angle Φ between the filament electrodes $9_u$ and $9_b$ of the upper-stage and lower-stage electron biprisms according to the invention of Japanese Patent Application No. 2005-027274 explained in FIG. 2 in a shown form corresponding to FIG. 1. The filament electrode $9_b$ of the lower-stage electron biprism is drawn in the landscape-orientation to show that there is the azimuth angle Φ between the filament electrode $9_b$ of the lower-stage electron biprism and the filament electrode $9_u$ of the upper-stage electron biprism.

In FIG. 2, the filament electrode $9_u$ of the upper-stage electron biprism coincides with X-axis. Those corresponding to the components shown in FIG. 1 are indicated by the same reference numerals in FIGS. 2 and 3. An ellipse indicated by a dashed line of FIG. 2 schematically shows the position of one wavefront in each position. A square indicated by a dashed line schematically shows the second image plane of the electron source 35.

The relation between the azimuth angle Φ between the filament electrodes $9_u$ and $9_b$ of the upper-stage and lower-stage electron biprisms and the azimuth θ of the interference fringes obtained is changed by the arrangement of the optical system and is changed by the applied voltage to the filament electrode of the upper-stage electron biprism. This is led by geometric optics. The relational equations of the optical system according to Japanese Patent Application No. 2005-027274 are expressed as Equations (5), (6), and (7). All of them show the relation projected onto the object plane where the specimen is positioned. The letters in the respective equations are as described in FIGS. 1 to 3 and the above description.

$$S_{Obj} = \frac{1}{M_M} \cdot \frac{1}{M_{Obj}} \cdot \frac{D_b \lambda}{\sqrt{\left(\frac{b_s}{a_s}D_u \alpha_u\right)^2 + (D_b - L_b)^2 \alpha_b^2 + 2\left(\frac{b_s}{a_s}D_u \alpha_u\right)(D_b - L_b)\alpha_b \cos\Phi}} \quad \text{[Equation 5]}$$

$$W_{Obj} = \frac{1}{M_M} \cdot \frac{1}{M_{Obj}} \cdot 2\alpha_b L_b \cdot \cos\Phi - \frac{1}{M_{Obj}} d_u \qquad \text{[Equation 6]}$$

$$\theta_{Obj} = \text{Tan}^{-1}\left[\frac{(D_b - L_b)\alpha_b \sin\Phi}{\left(\frac{b_3}{a_3}D_u\alpha_u\right) + (D_b - L_b)\alpha_b \sin\Phi}\right] \qquad \text{[Equation 7]}$$

By these equations, in the case of the optical system which can independently control the interference area width W and interference fringe spacing s perfectly described in Japanese Patent Application No. 2004-004156, that is, in the case of ($D_b-L_b=0$) in which the filament electrode $9_b$ of the lower-stage electron biprism is located on the image plane of the electron source 35, the azimuth θ of the interference fringes recorded onto a hologram is zero regardless of the azimuth angle Φ between the filament electrodes of both the biprisms. Conversely, this means that the accuracy for adjusting the azimuth angle Φ between the filament electrodes of the two electron biprisms is not much important in the case of the conditions.

Embodiment 1

FIG. 4 is a schematic diagram showing an optical system of Embodiment 1 of an interferometer having upper-stage, intermediate-stage, and lower-stage electron biprisms of the present invention. It shows a three-dimensional structure easily to understand the azimuth angles $\Phi_1$ and $\Phi_3$ among the filament electrodes of the three electron biprisms and to explain formation of interference fringes obtained on the observation plane 11. As apparent by comparing FIG. 4 with FIG. 2, in Embodiment 1, a magnifying lens system is added in the lower portion of the objective lens system and in the upper portion of the upper-stage electron biprism corresponding to the intermediate position of the optical system of the double-biprism electron interferometer, and a new electron biprism is located in the object plane of the added magnifying lens system (the image plane of the objective lens system). The electron source 1, the optical axis 2, the specimen 3, the objective lens system 5, the first image plane of the electron source 7 just above the upper-stage electron biprism, the observation plane 11, the object wave 21, and the reference wave 23 explained FIGS. 1, 2, and 3 are indicated by the same reference numerals in FIG. 4. In order to avoid misunderstanding and complication, the later description and equations are defined again in FIG. 4 and the drawing thereafter. Here, in order of the direction in which the electron beam flows, the filament electrode of the upper-stage electron biprism is $9_1$, the filament electrode of the intermediate-stage electron biprism is $9_2$, and the filament electrode of the lower-stage electron biprism is $9_3$. The diameters of the filament electrodes are $d_1$, $d_2$, and $d_3$, respectively.

In FIG. 4, the reference numeral 61 denotes a first image plane by the objective lens system 5, and the reference numeral 62 denotes a specimen image on the first image plane 61. The filament electrode $9_1$ of the upper-stage electron biprism is provided on the first image plane 61. Here, an azimuth angle formed between the filament electrode $9_1$ and X-axis is $\Phi_1$. The reference numeral 63 denotes a first magnifying lens system having one or more lenses provided at the later stage of the first image plane 61, and $\alpha_1$ denotes a deflection angle of the electron beam by the filament electrode $9_1$ of the upper-stage electron biprism. The reference numeral 65 denotes a second image plane of the electron source by the first magnifying lens system 63. Split of real images of the electron source 66 and 67 are occurred by deflection of the electron beam by the filament electrode $9_1$ of the upper-stage electron biprism. The reference numeral 71 denotes a second image plane by the first magnifying lens system 63. The reference numeral 72 denotes a specimen image on the second image plane 71. The filament electrode $9_2$ of the intermediate-stage electron biprism is provided on the second image plane 71. Here, the filament electrode $9_2$ is provided on X-axis. The azimuth angle formed between the filament electrode $9_1$ of the upper-stage electron biprism and the filament electrode $9_2$ of the intermediate-stage electron biprism is $\Phi_1$.

The reference numeral 73 denotes a second magnifying lens system having one or more lenses provided at the later stage of the second image plane 71, and $\alpha_2$ denotes a deflection angle of the electron beam by the filament electrode $9_2$ of the intermediate-stage electron beam biprism. The reference numeral 75 denotes a third image plane of the electron source by the second magnifying lens system 73. Four real images of the electron source are formed on the third image plane of the electron source 75 by the filament electrode $9_1$ of the upper-stage electron biprism and the filament electrode $9_2$ of the intermediate-stage electron biprism. Electron source images 76 and 78 are split from the electron-source image 67 on the second image plane of the electron source 65. Electron-source images 77 and 79 are split from the electron-source image 66 on the second image plane of the electron source 65. The four real images of the electron source form four virtual images of the electron source 81, 82, 83, and 84 by the deflection by the filament electrode $9_3$ of the lower-stage electron biprism.

In FIG. 4, the reference numeral 91 denotes a plane in space in which the filament electrode $9_3$ of the lower-stage electron biprism is located. In geometric optics, deflection by the lower-stage electron biprism occurs on this plane. The reference numeral 93 denotes a wavefront just before deflection and made by the object wave on the plane 91, and the reference numeral 94 denotes a wavefront of the reference wave. The two wavefronts are superimposed together on the observation plane 11 to form interference fringes. The azimuth angle formed between the filament electrode $9_3$ of the lower-stage electron biprism on the plane 91 and X-axis is $\Phi_3$. The azimuth angle formed between the filament electrode $9_3$ of the lower-stage electron biprism and the filament electrode $9_2$ of the intermediate-stage electron biprism is $\Phi_3$. $\alpha_3$ denotes a deflection angle of the electron beam by the filament electrode $9_3$ of the lower-stage electron biprism. The electron beam deflected by the filament electrodes of the three electron biprisms forms a specimen image 101 and interference fringes 102, shades 103 and 104 of the filament electrode $9_1$ of the upper-stage electron biprism, and shades 105 and 106 of the filament electrode $9_2$ of the intermediate-stage electron biprism on the observation plane 11.

FIG. 5 is a schematic diagram, in a shown form corresponding to FIGS. 1 and 3, to understand more easily the geometric relation between the positions of the filament electrodes of the respective electron biprisms, the objective lens system and the magnifying lens systems in FIG. 4, and the depth is omitted. The filament electrode $9_1$ of the upper-stage electron biprism and the filament electrode $9_3$ of the lower-stage electron biprism are drawn in the landscape-orientation to show that the azimuth angle between the filament electrode $9_1$ of the upper-stage electron biprism, the filament electrode $9_3$ of the lower-stage electron biprism, and the filament electrode $9_2$ of the intermediate-stage electron biprism. The filament electrode $9_1$ of the upper-stage electron biprism is located on the first image plane 61 just below the objective lens system 5. The filament electrode $9_2$ of the intermediate-stage electron biprism is located on the second image plane 71 just below the first magnifying lens system 63 having one or more lenses. The filament electrode $9_3$ of the lower-stage electron biprism is arranged between the third image plane of the electron source 75 just below the second magnifying lens system 73 having one or more lenses and the third image plane 92. An imaging lens system including a third magnifying lens 42, a fourth magnifying lens system 43, and a projection lens 44 is provided on the downstream side in the traveling direction of the electron beam from the third image plane 92, and the observation plane 11 is provided on the further downstream side. The configuration of the optical system below the third image plane 92 does not affect the function of the triple-biprism electron interferometer. The specimen images on the respective image planes in the drawing are indicated by thick arrows.

The relational equations of the optical system shown in FIGS. 4 and 5 can be derived by geometric optics relatively easily. In the relation between the specimen image 101 and the interference fringes 102, the shades 103 and 104 of the filament electrode $9_1$ of the upper-stage electron biprism, and the shades 105 and 106 of the filament electrode $9_2$ of the intermediate-stage electron biprism, which are formed on the observation plane 11 by the electron beam deflected by the filament electrode 9 of the three electron biprisms, the components and the parameters are defined as follows to express the relation after backprojection onto the objective plane as Equations (8) to (12). (The shades of the filament electrodes are represented as the terms of subtraction in the interference area widths $W_x$ and $W_y$ shown in Equations (10) and (11).) For simplification, the magnifying lens system and the projection lens system after the third image plane 92 are omitted. Here, $M_{Obj}$ is a magnification by the objective lens system 5 to the specimen 3, $M_{M1}$ is a magnification by the first magnifying lens system 63 to the specimen image 62, $M_{M2}$ is a magnification by the second magnifying lens system 73 to the specimen image 72, $a_1$ is a distance between the objective lens system 5 and the electron source 1, $b_1$ is a distance between the objective lens system 5 and the first image plane of the electron source 7, $D_1$ is a distance between the first image plane of the electron source 7 and the first image plane (the filament electrode $9_1$ of the upper-stage electron biprism), $a_2$ is a distance between the first image plane of the electron source 7 and the first magnifying lens system 63, $b_2$ is a distance between the first magnifying lens system 63 and the second image plane of the electron source 65, $a_3$ is a distance between the second image plane of the electron source 65 and the second magnifying lens system 73, $D_2$ is a distance between the second image plane of the electron source 65 and the second image plane 71 (the filament electrode $9_2$ of the intermediate-stage electron biprism), $b_3$ is a distance between the second magnifying lens system 73 and the third image plane of the electron source 75, $D_3$ is a distance between the third image plane of the electron source 75 and the observation plane 11, and $L_3$ is a distance between the third image plane 91 (the filament electrode $9_3$ of the lower-stage electron biprism) and the observation plane 11. On the observation plane 11, the widths of the interference fringes 102 in the X-axis and Y-axis directions are $W_x$ and $W_y$, and an azimuth of the interference fringes 102 with respect to X-axis is $\theta$.

$$S_{Obj} = \frac{1}{M_{Obj}} \cdot \frac{1}{M_{M1}} \cdot \frac{1}{M_{M2}} \cdot \frac{D_3 \lambda}{2 r_3} \quad \text{[Equation 8]}$$

where $r_3$ is defined by Equation (9).

$$r_3 = \left\{ \left( \frac{b_3}{a_3} \frac{b_2}{a_2} D_1 \alpha_1 \sin\Phi_1 + (D_3 - L_3) \alpha_3 \sin\Phi_3 \right)^2 + \right.$$
$$\left( \frac{b_3}{a_3} \frac{b_2}{a_2} D_1 \alpha_1 \cos\Phi_1 + \frac{b_3}{a_3} D_2 \alpha_2 + \right.$$
$$\left. \left. (D_3 - L_3) \alpha_3 \cos\Phi_3 \right)^2 \right\}^{\frac{1}{2}} \quad \text{[Equation 9]}$$

$$W_{Objx} = \quad \text{[Equation 10]}$$
$$\frac{1}{M_{Obj}} \cdot \frac{1}{M_{M1}} \cdot \frac{1}{M_{M2}} \cdot 2\alpha_3 L_3 (\sin\Phi_1 \sin\Phi_3 + \cos\Phi_1 \cos\Phi_3) -$$
$$\left( \frac{d_1}{M_{Obj}} + \frac{1}{M_{Obj}} - \frac{1}{M_{M1}} d_2 \cos\Phi_1 \right)$$

$$W_{Objy} = \quad \text{[Equation 11]}$$
$$\frac{1}{M_{Obj}} \cdot \frac{1}{M_{M1}} \cdot \frac{1}{M_{M2}} \cdot 2\alpha_3 L_3 \cos\Phi_3 - \frac{d_2}{M_{Obj} M_{M1} \sin\Phi_1}$$

$$\theta_{Obj} = \operatorname{Tan}^{-1} \left[ \frac{\frac{b_3}{a_3} \frac{b_2}{a_2} D_1 \alpha_1 \sin\Phi_1 + (D_3 - L_3) \alpha_3 \sin\Phi_3}{\frac{b_3}{a_3} \frac{b_2}{a_2} D_1 \alpha_1 \cos\Phi_1 + \frac{b_3}{a_3} D_2 \alpha_2 + (D_3 - L_3) \alpha_3 \cos\Phi_3} \right] \quad \text{[Equation 12]}$$

FIG. 6 is a schematic diagram in which the geometric relation among the filament electrodes of the three electron biprisms is projected onto the third image plane 92. For simplification, the filament electrode $9_2$ of the intermediate-stage electron biprism is indicated just on X-axis, and the azimuth angles of the filament electrode $9_1$ of the upper-stage electron biprism and the filament electrode $9_3$ of the lower-stage electron biprism from X-axis are $\Phi_1$ and $\Phi_3$, respectively. For the positions along the optical axis, as described above, the filament electrodes of the upper two electron biprisms are located in the image plane of the specimen of the lens systems. The filament electrode $9_3$ of the lower-stage electron biprism may be in any position on the optical system which perfectly enter the shadow area of the filament electrodes $9_2$ and $9_1$ of the intermediate-stage and upper-stage electron biprisms when $\Phi_3=0°$ or $\Phi_3=\Phi_1$.

The shape of the interference area obtained by the present invention is a parallelogram having the azimuth angle $\Phi_1$ formed by the filament electrodes of the upper two electron biprisms and the ratio of $W_{Objx}$ and $W_{Objy}$ ($W_{Objx}/W_{Objy}$) determined by Equations (10) and (11).

FIGS. 7(A) to 7(D) are experimental results showing interference area obtained by fixing the azimuth at $\Phi_3=45°$ and by changing $\Phi_1$. FIG. 7(A) shows $\Phi_1=50°$, FIG. 7(B) shows $\Phi_1=70°$, FIG. 7(C) shows $\Phi_1=90°$, and FIG. 7(D) shows $\Phi_1=110°$, respectively. In the applied voltages to the filament electrodes in a series of experiments, the upper-stage electron biprism is held to $V_1=30V$, the intermediate-stage electron biprism is held to $V_2=30V$, and the lower-stage electron biprism is held to $V_3=160V$, respectively. The shades 103 and 104 of the filament electrode $9_1$ of the upper-stage electron biprism are shown by upwardly leftward, thick black lines. The shades 105 and 106 of the filament electrode $9_2$ of the intermediate-stage electron biprism are shown by upwardly rightward, thick black lines. The shape of the parallelogram of the interference area is found to be changed with azimuth of the filament electrode $9_1$ of the upper-stage electron beam biprism. As $\Phi_3=45°$ is fixed, the interference area (which is the same as the interference area by the conventional single biprism interferometer) in white band outside the parallelogram-shaped interference area provided by the filament electrode $9_3$ of the lower-stage electron biprism is not moved. However, the shades 103 and 104 of the filament electrode $9_1$ of the upper-stage electron biprism are rotated with azimuth rotation. Based on Equations (8), (9), and (12), the interference fringe spacing s and the azimuth θ of the interference area surrounded by the shades of the filament electrodes are changed. This will be described later with the experimental results.

In practical use such as convenience of operation, it is advantageous that the filament electrodes of the upper two electron biprisms be orthogonal to each other ($\Phi_1=90°$). FIGS. 8(A) to 8(C) are experimental results showing interference area obtained by fixing azimuth angle between the filament electrode $9_1$ of the upper-stage electron biprism and the filament electrode $9_2$ of the intermediate-stage electron biprism in the state that they are orthogonal to each other ($\Phi_1=90°$), and by changing the azimuth angle $\Phi_3$ formed by the filament electrode $9_2$ of the intermediate-stage electron biprism and the filament electrode $9_3$ of the lower-stage electron biprism, and observing the shape change of an interference area. FIG. 8(A) shows $\Phi_3=30°$, FIG. 8(B) shows $\Phi_3=45°$, and FIG. 8(C) shows $\Phi_3=60°$, respectively. The applied voltages to the filament electrodes are held to $V_1=20V$, $V_2=20V$, and $V_3=120V$, respectively. While two sides formed by the interference area maintain the orthogonal relation with rotation of the filament electrode $9_3$ of the lower-stage electron biprism, and the lengths of the sides are changed, that is, the interference area is changed in such a manner of rectangle to square to rectangle. In a series of the experimental results in FIG. 8, the interference fringe spacing s and the azimuth θ of the interference area surrounded by the shades of the filament electrodes are also changed, which will be described later, as described above.

FIGS. 9(A) to 9(D) show experimental results obtained by the dependence of the applied voltage $V_3$ on the filament electrode of the lower-stage electron biprism in the shape of the interference area when the azimuth angles among the filament electrodes of the electron biprisms are constant. FIG. 9(A) shows $V_3=0V$, FIG. 9(B) shows $V_3=40V$, FIG. 9(C) shows $V_3=90V$, and FIG. 9(D) shows $V_3=140V$, respectively. The azimuth angles among the filament electrodes are $\Phi_1=90°$ and $\Phi_3=30°$.

As shown in FIG. 9(A), in $V_3=0V$ of the filament electrode of the lower-stage electron biprism, the shades of the upper two electron biprisms are orthogonal to each other and no interference areas are formed. At this time, the shades 103 and 104 or 105 and 106 of the upper-stage or intermediate-stage filament electrode are united. As the applied voltage $V_3$ to the filament electrode of the lower-stage electron biprism is increased, the electron wave is deflected to be mutually opposite to the lower-stage filament electrode (FIG. 9(B)). An interference area starts occurring with overlap of wavefront (FIG. 9(C)). The interference area is found to be enlarged while maintaining similar shapes. The applied voltage $V_3$ to the filament electrode of the lower-stage electron biprism can control the size of the interference area.

The series of experimental results in FIG. 9 show the idea of control of the electron wave according to the present invention well. The wavefront is divided into four by the upper two electron biprisms and the azimuth angle $\Phi_3$ of the lower-stage filament electrode $9_3$ selects two waves of these to interfere with each other. The upper right and lower left waves in FIG. 9 are selected. When two waves diagonally opposite to each other are selected, independent control of all interference parameters as the feature of the present invention can be done. When the right and left waves or the upper and lower waves are selected, that is, $\Phi_3=0°$ or $\Phi_3=90°$, the control characteristic of the interference phenomenon coincides with Japanese Patent Application No. 2004-004156. The shape (aspect ratio) of the interference area by the two selected waves is controlled by the azimuth angle $\Phi_3$ between the filament electrodes of the intermediate-stage electron biprism and the filament electrode of the lower-stage electron biprism, and the size of the interference area is controlled by the applied voltage $V_3$. These are already described. The interference fringe spacing s and the azimuth θ obtained at this time can be controlled by the applied voltages to the filament electrodes of the upper two electron biprisms (described later). Such idea is very effective in practical use for determining the experimental conditions in an experiment using this optical system.

In the experimental results shown in FIGS. 7, 8, and 9, Fresnel fringes generated by the filament electrode $9_3$ of the lower-stage electron biprism are only observed outside the interference area. The influence on the inside of the observation area surrounded by the filament electrode $9_1$ of the upper-stage biprism and the filament electrode $9_2$ of the intermediate-stage electron biprism is small to the level at which it can be substantially neglected. This is very effective in practical use. When the azimuth angle of the filament electrode $9_3$ of the lower-stage electron biprism is $\Phi_3=0°$ or $\Phi_3=\Phi_1$, the optical system of the triple-biprism electron interferometer according to the present invention coincides with the optical system of the double-biprism electron interferometer. In principle, no Fresnel fringes as a problem are generated.

As described above, control of the interference fringes within the interference area formed by the upper two electron biprisms will be considered. For simplification, the case where the filament electrodes $9_1$ and $9_2$ of the upper two electron biprisms are orthogonal to each other ($\Phi_1=90°$) will be assumed for description. This can be treated likewise in a general case. As shown in FIG. 4, fringe spacing $s_x$ and $s_y$ in the X-axis and Y-axis directions will be studied. The new two parameters can be expressed as Equations (13) and (14) using the interference fringe spacing s and the azimuth θ of the interference fringes.

$$S_{Objx} = \frac{S_{Obj}}{\sin\theta_{Obj}} \qquad \text{[Equation 13]}$$
$$= \frac{1}{M_{Obj}} \cdot \frac{1}{M_{M1}} \cdot \frac{1}{M_{M2}}.$$

-continued $$S_{Objy} = \frac{S_{Obj}}{\cos\theta_{Obj}} \quad \text{[Equation 14]}$$

$$= \frac{1}{M_{Obj}} \cdot \frac{1}{M_{M1}} \cdot \frac{1}{M_{M2}} \cdot$$

$$\frac{D_3\lambda}{2\left(\frac{b_3}{a_3}D_2\alpha_2 + (D_3 - L_3)\alpha_3\cos\Phi_3\right)}$$

When the operating conditions of the lower-stage electron biprism (the applied voltage $V_3$ (the deflection angle $\alpha_3$) and the azimuth angle $\Phi_3$) are determined, $s_x$ is dependent only on the applied voltage to the upper-stage electron biprism (the deflection angle $\alpha_1$) controlling interference in the X-axis direction, and $s_y$ is dependent only on the applied voltage to the intermediate-stage biprism (the deflection angle $\alpha_2$) controlling interference in the Y-axis direction. This is on the basis of, when filament electrodes $9_1$ and $9_2$ of the upper two electron biprisms are orthogonal to each other ($\Phi_1$=90°), providing deflection on the wavefront independently in the X-axis and Y-axis directions by the applied voltages to the filament electrodes. When the sizes are changed without changing the ratio of $s_x$ and $s_y$, only the interference fringe spacing s can be controlled. When only the ratio is changed without changing the magnitude of the square sum of $s_x$ and $s_y$, only the azimuth θ of the interference fringes can be controlled. The interference fringe spacing s and the azimuth θ of the interference fringes can be controlled independently by the applied voltages to the upper-stage and intermediate-stage electron biprisms based on Equations (15) and (16).

$$S_{Obj} = \sqrt{S_{Objx}^2 + S_{Objy}^2} \quad \text{[Equation 15]}$$

$$\theta_{Obj} = \text{Tan}^{-1}\left[\frac{S_{Objy}}{S_{Objx}}\right] \quad \text{[Equation 16]}$$

$$= \text{Tan}^{-1}\left[\frac{\frac{b_3}{a_3}\frac{b_2}{a_2}D_1\alpha_1 + (D_3 - L_3)\alpha_3\sin\Phi_3}{\frac{b_3}{a_3}D_2\alpha_2 + (D_3 - L_3)\alpha_3\cos\Phi_3}\right]$$

FIG. 10 shows the experimental result obtained by independently changing the interference fringe spacings ($s_x$, $s_y$) in the X-axis and Y-axis directions. To clearly observe the interference fringe spacing s and the azimuth θ in the drawing, the center portion in the interference area shown in FIG. 9(D) is extracted and enlarged. Three interferograms arrayed in the horizontal direction show the results obtained by controlling only the applied voltage $V_2$ to the intermediate-stage electron biprism to 30V, 60V, and 90V to independently change only the interference fringe spacing $s_y$. As only the interference fringe spacing $s_y$ is changed, the azimuths θ of the interference fringes are all different. When the interference fringes and the connection parts of the three interferograms are seen, they are kinked lines and keep constant with the fringe spacing $s_x$ in the vertical direction. The three interferograms arrayed in the vertical direction show the results obtained by controlling only the applied voltage $V_1$ to the upper-stage electron biprism to 30V, 60V, and 90V to independently change only the interference fringe spacing $s_x$. As only the interference fringe spacing $s_x$ is changed, the azimuths θ of the interference fringes are all different. When the interference fringes and the connection parts of the three interferograms are seen, they are also kinked lines and keep constant with the fringe spacing $s_y$ in the horizontal direction. That is, independent control of the interference fringe spacings ($s_x$, $s_y$) in the X-axis and Y-axis directions can be done. In these interferograms, as only either one of $s_x$ and the interference fringe spacing $s_y$ is changed, the azimuths θ of the interference fringes are all different. As shown in Equation (16), the azimuth θ of the interference fringes is determined by the ratio of the fringe intervals in the respective directions. Accordingly, the applied voltages to the filament electrodes of the upper two electron biprisms are properly selected to allow independent control.

FIGS. 11(A) to 11(C) are holograms as experimental examples obtained by controlling the applied voltage $V_1$ to the upper-stage electron biprism and the applied voltage $V_2$ to the intermediate-stage electron biprism and changing the interference fringe spacing in the state that the azimuth θ of the interference fringes is maintained constant (θ=−45°). Small crystals of magnesium oxide are used as a specimen. In the interference fringe spacings, FIG. 11(A) shows $s_{Obj}$=5 nm, FIG. 11(B) shows $s_{Obj}$=4 nm, and FIG. 11(C) shows $s_{Obj}$=3 nm, respectively. The black portions around the holograms are the shades of the filament electrodes of the upper-stage electron biprism and the intermediate-stage electron biprism.

FIGS. 12(A) to 12(C) are also holograms as experimental examples obtained by controlling the applied voltage $V_1$ to the upper-stage electron biprism and the applied voltage $V_2$ to the intermediate-stage electron biprism and changing only the azimuth θ of the interference fringes in the state that the interference fringe spacing is maintained constant ($s_{Obj}$=4 nm). In the azimuths θ, FIG. 12(A) shows θ=−30°, FIG. 12(B) shows θ=−45°, and FIG. 12(C) shows θ=−60°, respectively.

The examples shown in FIGS. 11 and 12 show that adjustment of the interference fringe spacing and the azimuth which has been performed only at image reconstruction in the conventional electron holography can be directly done by an electron beam in an electron microscope.

Embodiment 2

In the optical system shown in FIGS. 4 and 5, when the magnification factor by the first magnifying lens system 63 is 1, relative correction by the magnification difference in the X-axis and Y-axis directions is unnecessary. Treating of an interference phenomenon is substantially equivalent and easy in the X-axis and Y-axis directions. When this idea is extended further, the filaments $9_1$ and $9_2$ of the upper two electron biprisms are provided on the first image plane 61, whereby an effect substantially equivalent to the triple-biprism electron interferometer explained in Embodiment 1 is found to be obtained by the same optical system of the double-biprism electron interferometer.

FIG. 13 is a schematic diagram of an optical system in which two filament electrodes corresponding to the filament electrode $9_1$ of the upper-stage biprism and the filament electrode $9_2$ of the intermediate-stage electron biprism of the triple-biprism electron interferometer explained in Embodiment 1 are orthogonal to each other to be mounted in the position of the upper-stage electron biprism, and the filament electrode $9_3$ of the lower-stage electron biprism is mounted on a plane 91. The same components as those shown in FIG. 2 and equal functions thereto are indicated by similar reference numerals in FIG. 13. Here, two filament electrodes corresponding to the filament electrode $9_1$ of the upper-stage electron biprism and the filament electrode $9_2$ of the intermediate-stage electron biprism are orthogonal to each other but are electrically insulated from each other so that the voltages are controlled independently.

As described earlier, the filament electrode $9_1$ of the upper-stage electron biprism and the filament electrode $9_2$ of the intermediate-stage electron biprism are orthogonal to each other for use, which is advantageous in practical use. The structure of Embodiment 2 can obtain the same effect as the interferometer obtained by the optical system of the triple-biprism electron interferometer in FIG. 4 of Embodiment 1 by the optical system of the double-biprism electron interferometer proposed in Japanese Patent Application No. 2005-027274, which is advantageous for producing the apparatus. When a charged particle beam of an electron microscope is used, the effect of an electric field is estimated to be slightly reduced in the portion at which the filament electrodes of the electron biprisms cross each other in the X-axis and Y-axis directions. The influence can be superimposed on the interference fringes in the corner portion of an interference area obtained. The center portion of the interference area can be used without being affected by the reduction of the intensity of the electric field or in the state that the influence is small to the extent of being neglected.

(Application to the Interferometer Using Light Beam)

The interferometer using an electron is mainly described above. As described in Japanese Patent Application No. 2004-004156, the present invention can be embodied in the optical interferometer using light beam. FIG. 14 is a schematic diagram showing an example in which three optical biprisms are arranged in place of the electron biprisms $9_1$, $9_2$, and $9_3$ of the optical system shown in FIG. 4 and beam stoppers for intercepting light beam are provided in the center positions (the ridge line or back side of the ridge line positions) of the upper-stage and intermediate-stage optical biprisms, respectively. In FIG. 14, the reference numerals $9'_1$, $9'_2$, and $9'_3$ respectively denote optical biprisms in place of the electron biprisms $9_1$, $9_2$, and $9_3$. Beam stoppers 95, 96, and 97 for intercepting light beam are arranged in the respective center positions (the ridge line or back side of the ridge line positions).

In the same idea, the optical system for realizing the present invention according to the two electron biprisms shown in FIG. 13 can be embodied in the interferometer using light beam. FIG. 15 is a schematic diagram of the optical system for realizing the present invention according to the two electron biprisms shown in FIG. 13 is the interferometer using light beam. Like FIG. 14, in place of the electron biprisms, the optical biprisms are located in the respective positions. As shown in FIG. 13, in the interferometer using an electron, two filament electrodes are orthogonal to each other in the upper-stage electron biprism. An optical device corresponding to this, a quadrangular-pyramid prism shown in FIG. 15 is considered. When the filament electrodes are orthogonal to each other and the deflection angles are the same in the X-axis and Y-axis directions, the quadrangular-pyramid prism is used. When the deflection functions are different, the quadrangular-pyramid prism whose shape is changed according to it is used. It is thus possible to constitute the interferometer using light beam equivalent to the charged particle beam. In FIG. 15, the reference numeral $9_{12}$ denotes an optical biprism in place of the electron biprisms $9_1$ and $9_2$ and the beam stoppers 95 and 96 for intercepting light beam are provided in the center positions (the ridge line or back side of the ridge line positions). The reference numeral $9'_3$ denotes an optical biprism in place of the electron beam biprism $9_3$ and the intercepting plate 97 for intercepting light is provided in the center position (the ridge line or back side of the ridge line positions).

As described in Japanese Patent Application No. 2004-004156, generally, the optical biprism cannot change a deflection angle α by controlling a voltage, unlike the electron biprism. The optical biprism need to be replaced according to the interference fringe spacing s and the interference area width W targeted. Therefore, the use is troublesome. However, a case in an optical biprism shape by glass is made and a gas is filled in it so that its pressure can be changed, that is, the mass density can be changed. Accordingly, the refraction factor of the optical biprism is changed to perform arbitrary angle deflection, or the reflection angles of two mirrors in place of one biprism are controlled, to expect the same effect as the electron biprism (for instance, K. Harada, K. Ogai and R. Shimizu: Technology Reports of The Osaka University 39, 117 (1989)). In the case of the quadrangular-pyramid prism $9_{12}$, a case having a partition wall in the prism on or under the beam stopper is made and the inner pressures are controlled, thereby to control the refraction factors of the optical biprisms independently.

SUMMARY

The present invention is a two-wave interference type interferometer in which the wavefront of the electron beam is divided into four by the filament electrode $9_1$ of the upper-stage electron biprism and the filament electrode $9_2$ of the intermediate-stage electron biprism so that one of the four waves is the object wave and that one of the other three waves is selected as the reference wave, thereby obtaining an interference image. The interference relation between the selected object wave and reference wave can be freely controlled.

The using procedure of the interferometer according to the present invention will be summarized below.

(1) An observed area of a specimen and a position in which a reference wave for observing it as an interference image are determined.

(2) The positions of the upper-stage and intermediate-stage electron biprisms and the relative azimuth angle $\Phi_1$ are determined to form the corresponding interference image. It is practical to select the orthogonal relation $\Phi_1=90°$ from the operability of an interference area and the interference fringes unless otherwise required.

(3) The azimuth angle $\Phi_3$ of the lower-stage biprism is adjusted to determine the shape (aspect ratio) of the interference area corresponding to the shape of the specimen.

(4) The applied voltage $V_3$ to the filament electrode of the lower-stage electron biprism is changed to determine the size of the interference area.

(5) The applied voltages $V_1$ and $V_2$ to the filament electrodes of the upper-stage electron biprism and the intermediate-stage electron biprism are changed to adjust the interference fringe spacing s and the azimuth θ of the interference fringes formed in the observed area to be optimum to the observed target.

(6) The interferogram (electron hologram) obtained by the above procedure is recorded to provide analysis such as reconstruction.

By the above procedure, the shape of the interference area ($W_x/W_y$, as the ratio of two sides $W_x$ and $W_y$, forming the area and the angle $\Phi_1$ formed by the two sides), the size of the interference area, the interference fringe spacing s, and the azimuth θ of the fringes can be controlled independently, and the interferogram under the arbitrary interference conditions can be directly observed and recorded by the optical system for recording the interferogram without image processing such as hologram reconstruction after image recording. Needless to say, these procedures and interference conditions are worked out depending on Equations (8) to (16).

The interference optical system of the present invention is the advanced type of the conventional optical system and can exhibit new functions while covering all advantages of the optical systems. According to the present invention, the following functions and effects can be expected.

(1) Making of an interference area shape according to the shape of a specimen:

The shape of an interference area necessary for making a hologram can be determined without wastefully deteriorating coherence of an electron beam.

(2) Formation of interference fringes having an arbitrary fringe spacing and azimuth within an interference area:

Interference fringes having optimum spacing and azimuth can be superimposed according to an observed target such as the shape of a specimen, the shape of a portion to be observed, the orientation of a lattice image, or the spatial size of the interference area. This can make and record a hologram in the optimum state in spatial resolution and phase resolution.

(3) Elimination of Fresnel fringes generation:

Generation of Fresnel fringes as the greatest and most serious noise source for a hologram is eliminated to exclude the influence on a hologram.

(4) Extension of the concept of the electron holography to two dimensions:

The shape of interference area, the interference fringe spacing, and the azimuth of the interference fringes can be controlled arbitrarily. The wavefront of an electron beam can be controlled and interfered substantially freely in a two-dimensional plane. This can be an electron interferometer which can perform an experiment while the interference phenomenon of the electron beam is compared with that of light beam.

The present invention establishes the means and method for improving the operability of the wavefront-splitting type interferometer to dramatically increase the degree of freedom of an interferogram obtained directly. That is, the operability and performance of the wavefront-splitting type interferometer approaches those of an amplitude-splitting type interferometer. In this meaning, the present invention is effective for introducing the wavefront-splitting type interferometer into the optical apparatus without being limited to the charged particle beam such as the electron beam.

INDUSTRIAL APPLICABILITY

According to the present invention, it is possible to realize the interferometer using an electron microscope, which allows independent control of parameters of the interference fringe spacing s, the azimuth θ, and the shape of the interference area by the arbitrary interference area widths ($W_x$, $W_y$). Superimposition of Fresnel fringes on to the interference area can be eliminated.

EXPLANATION OF REFERENCE NUMERALS

Figure 1:
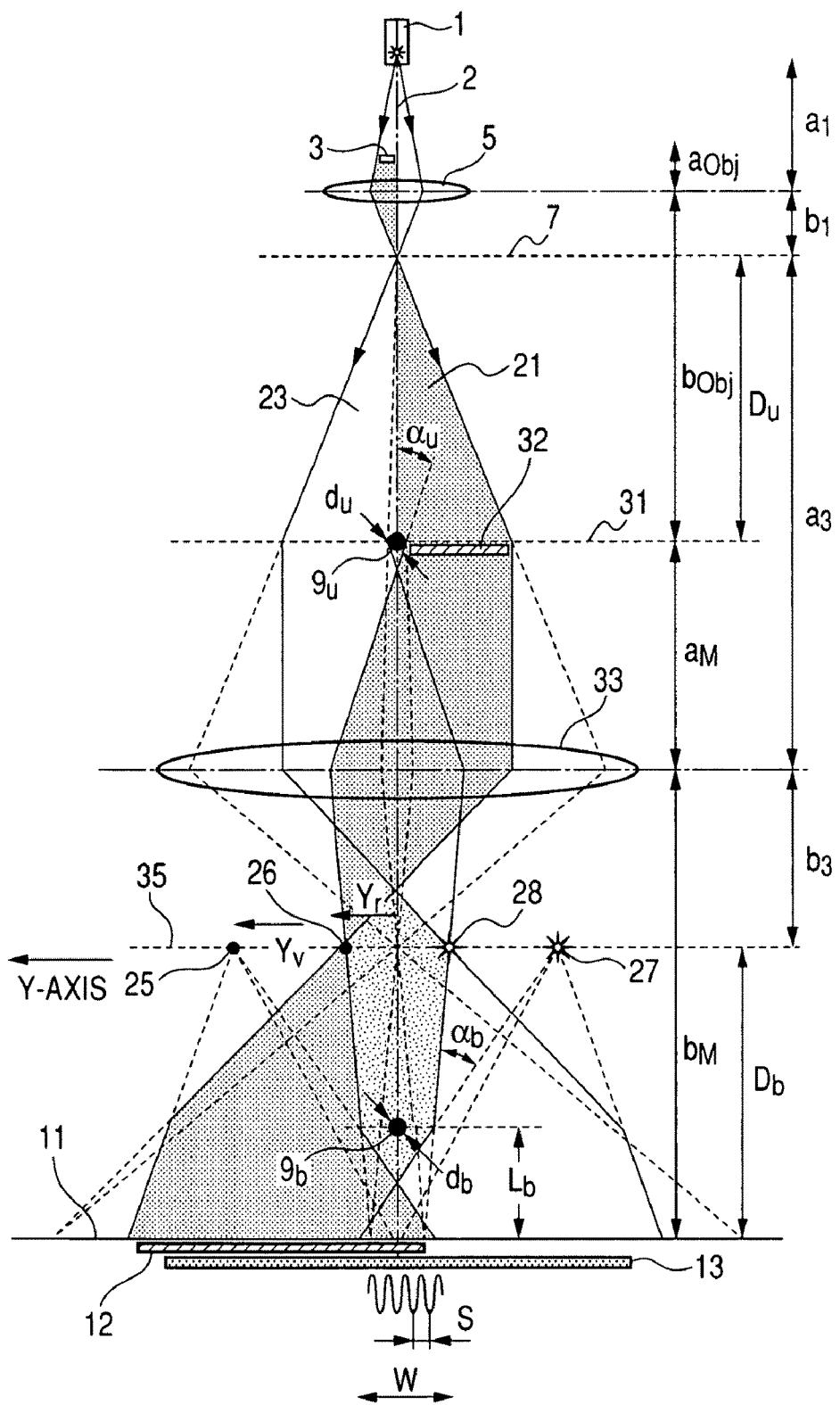
FIG. 1 is a schematic diagram of an interference optical system using electron biprisms explained in FIG. 3 of Japanese Patent Application No. 2004-004156.
Figure 2:
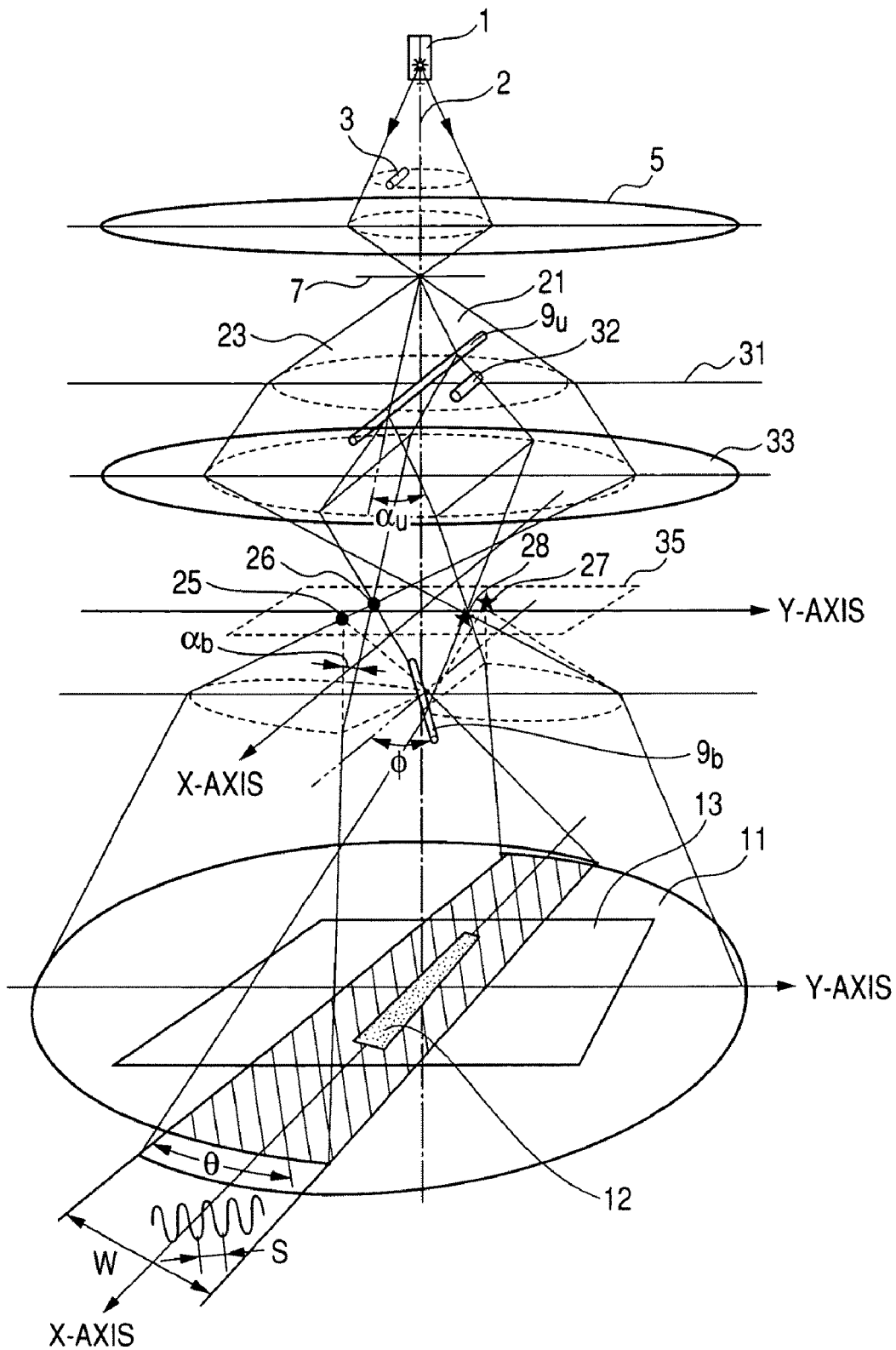
FIG. 2 is a schematic diagram of an optical system operating with an azimuth angle Φ between filament electrodes of upper-stage and lower-stage electron biprisms for explaining formation of interference fringes explained in FIG. 2 of Japanese Patent Application No. 2005-027274.
Figure 3:
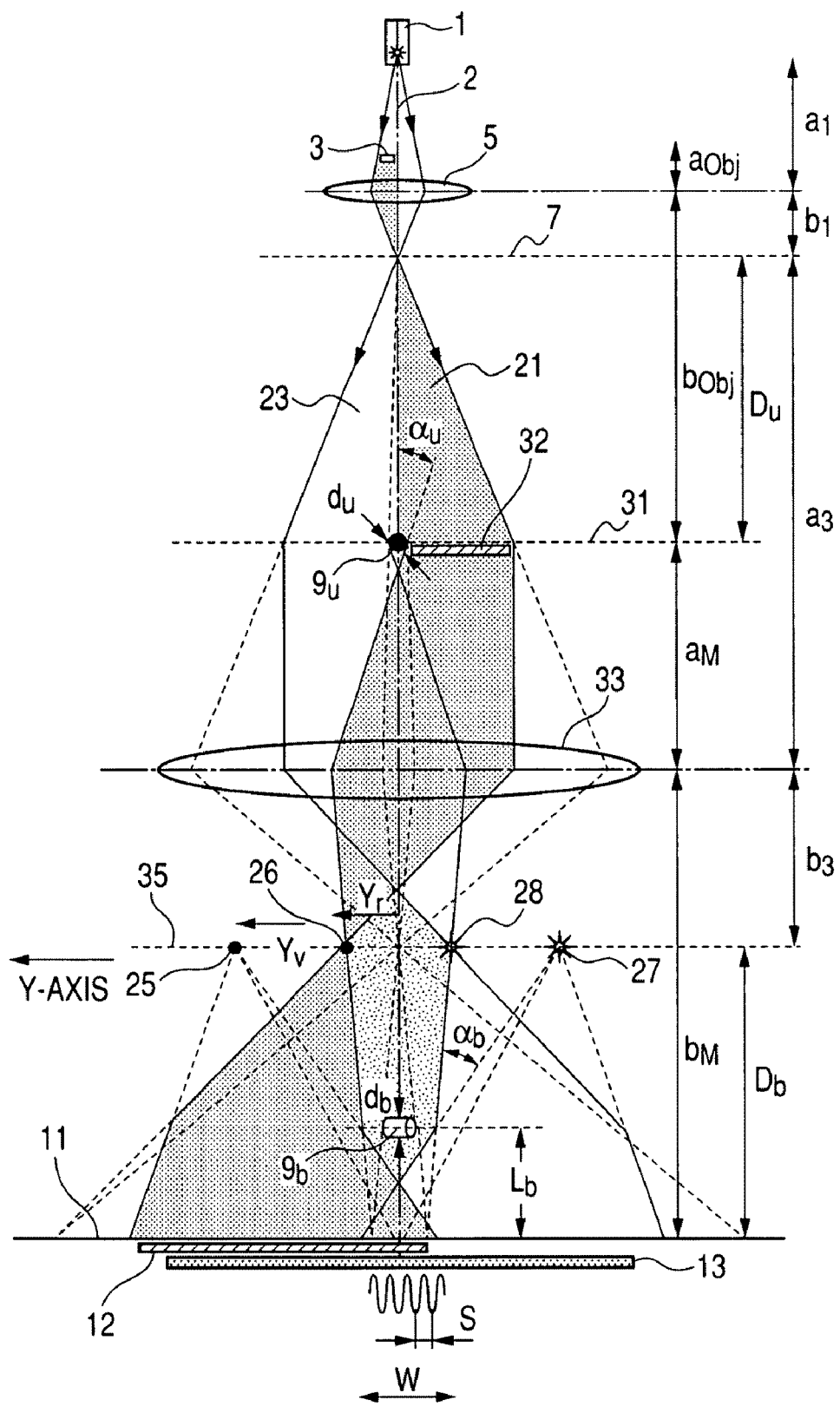
FIG. 3 is a schematic diagram of an optical system operating with the azimuth angle Φ between the filament electrodes $9_u$ and $9_b$ of the upper-stage and lower-stage electron biprisms according to the invention of Japanese Patent Application No. 2005-027274 explained in FIG. 2 in a shown form corresponding to FIG. 1.
Figure 4:
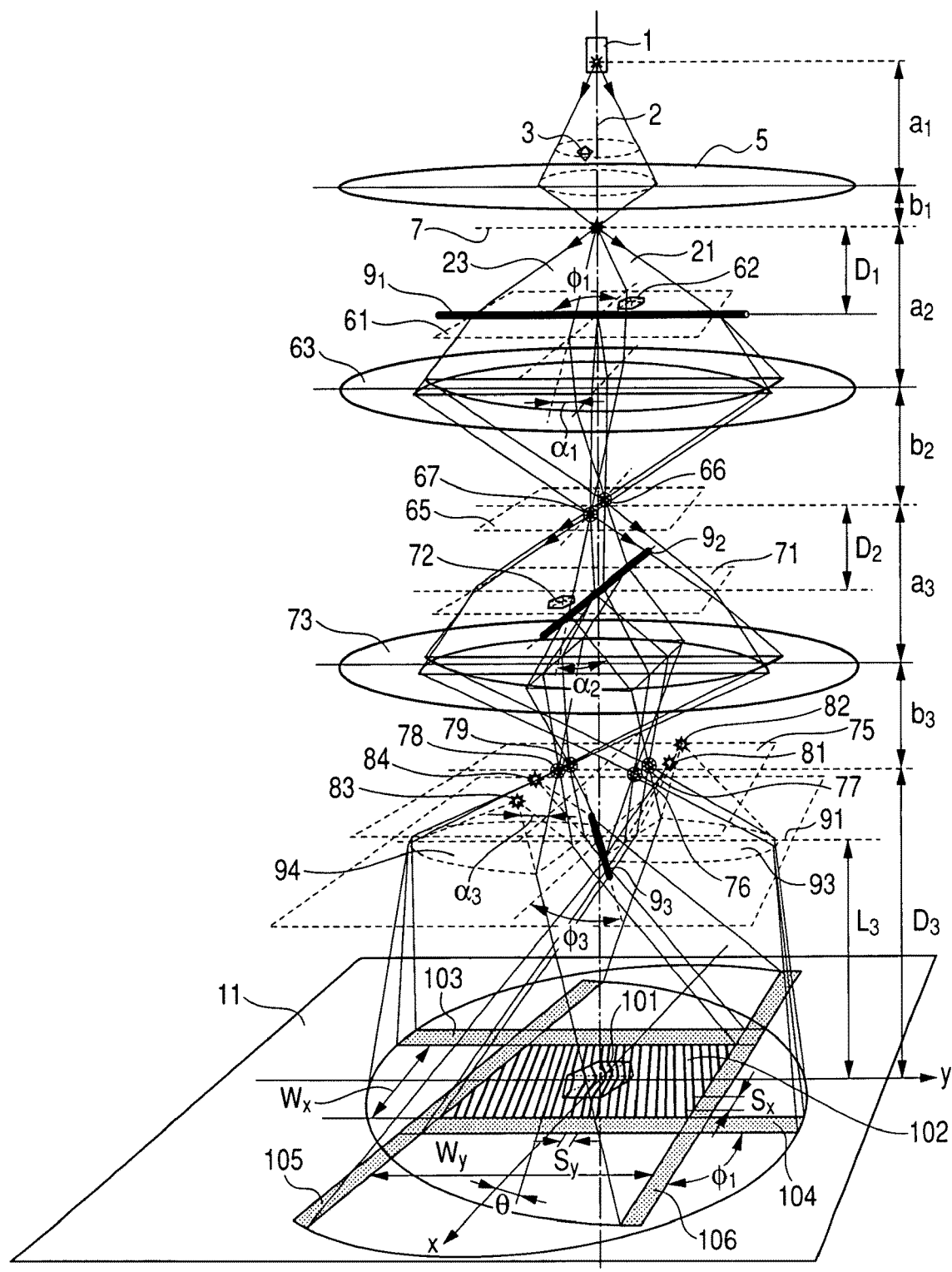
FIG. 4 is a schematic diagram of an optical system of Embodiment 1 of an interferometer having upper-stage, intermediate-stage, and lower-stage electron biprisms of the present invention.
Figure 5:
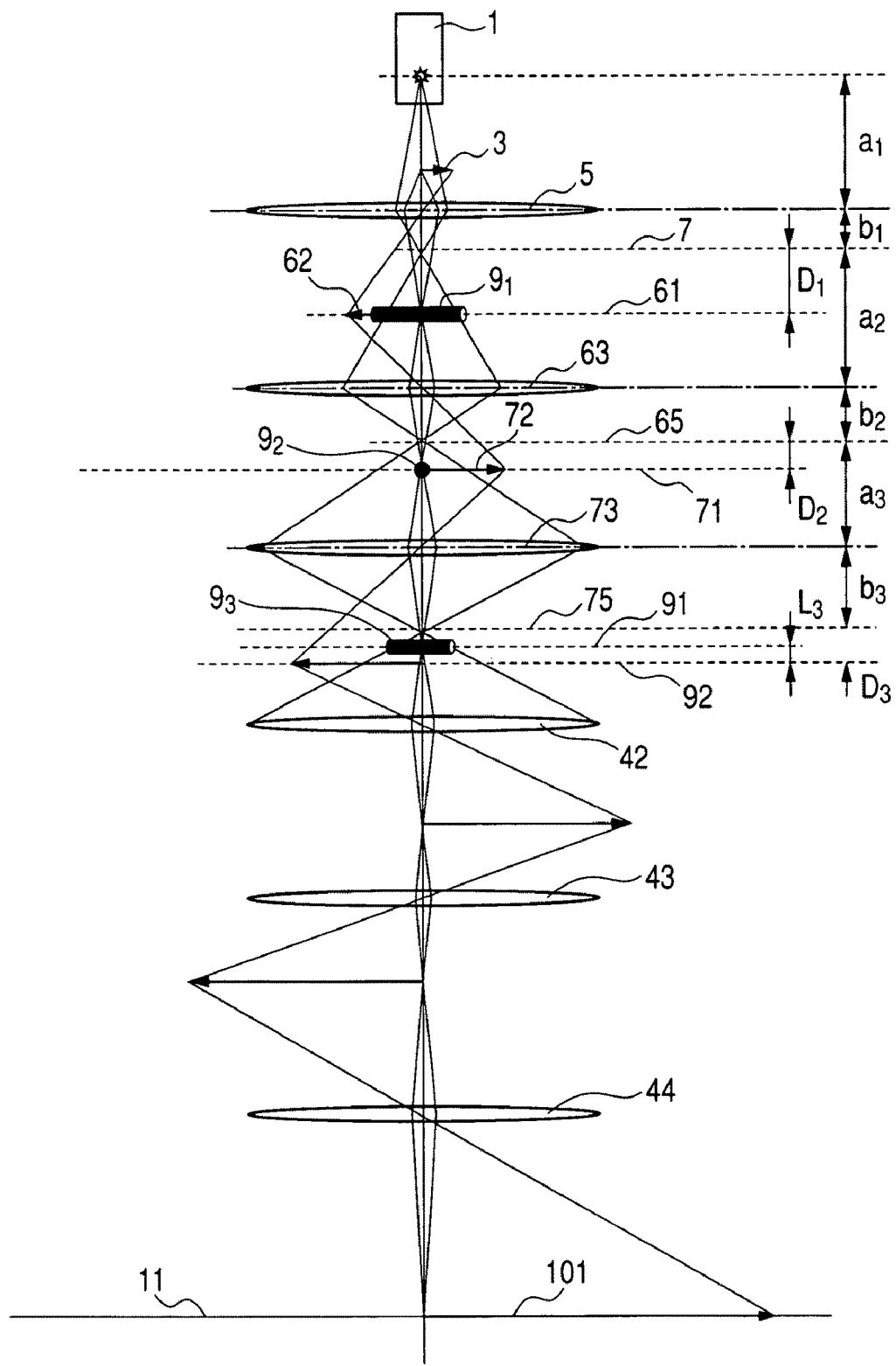
FIG. 5 is a schematic diagram, in a shown form corresponding to FIGS. 1 and 3, to understand more easily the geometric relation among the positions of the filament electrodes of the respective electron biprisms, the objective lens system in FIG. 4, and additional magnifying lens systems, and the depth is omitted.
Figure 6:
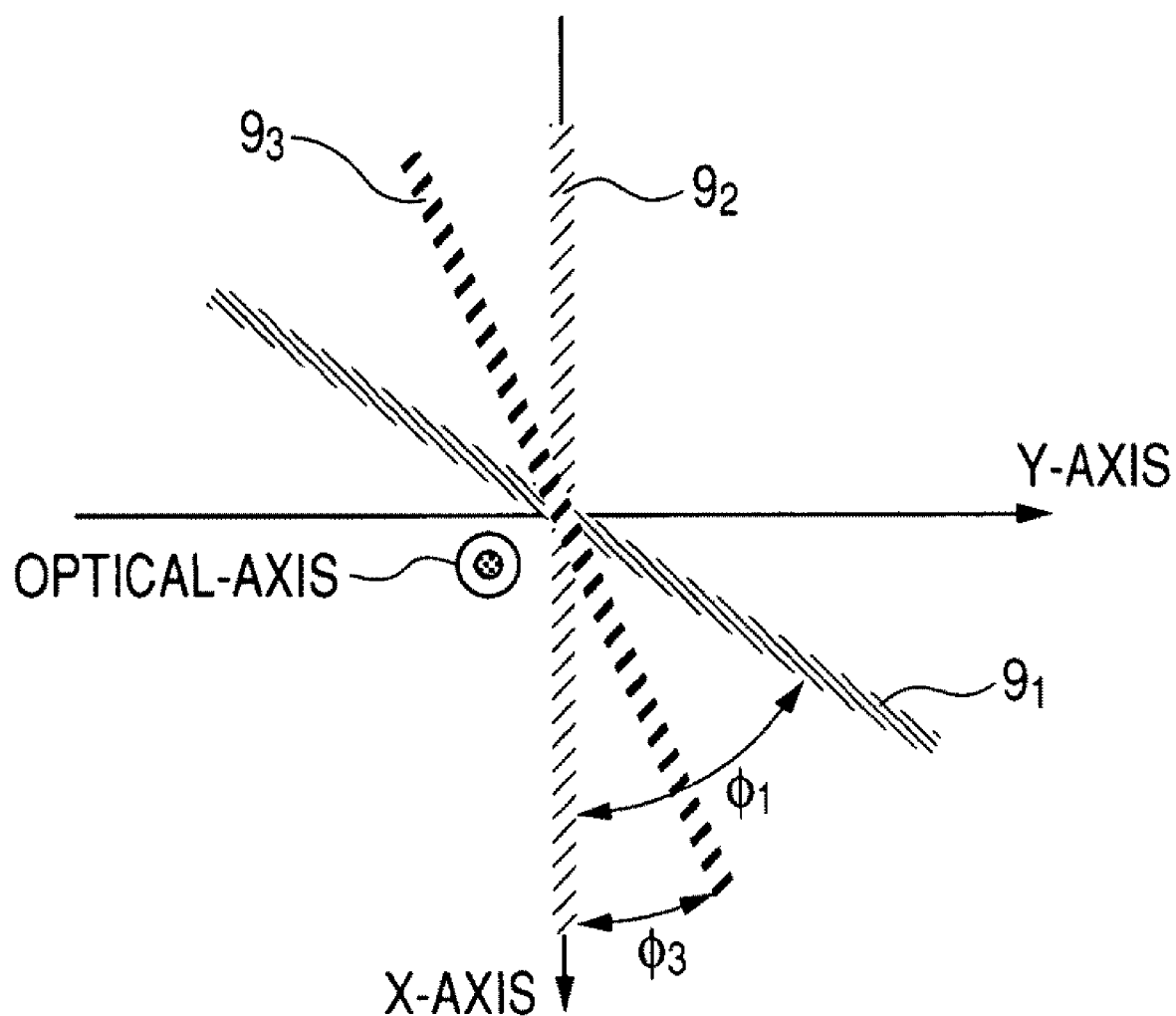
FIG. 6 is a diagram in which the azimuth-angular relation among the filament electrodes of the three electron biprisms is projected onto a third image plane 92.
Figure 7A:
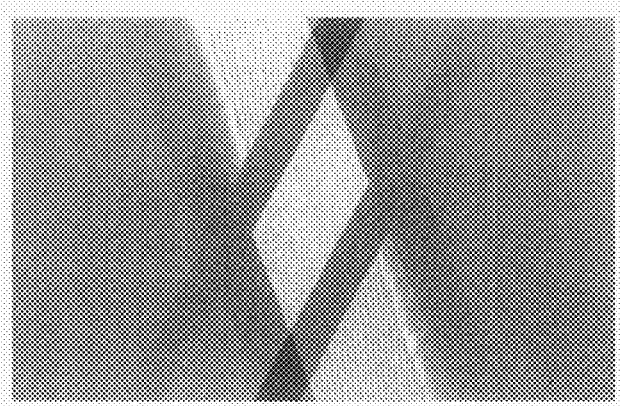
FIGS. 7(A) to 7(D) are experimental results showing interference area obtained by fixing the azimuth $\Phi_3=45°$ and by changing $\Phi_1$, respectively.
Figure 7B:
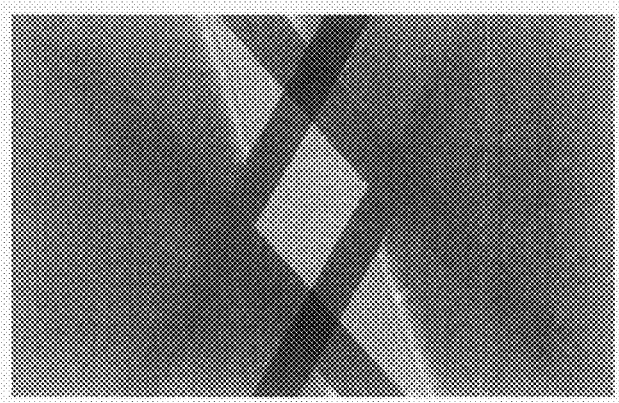
Figure 7C:
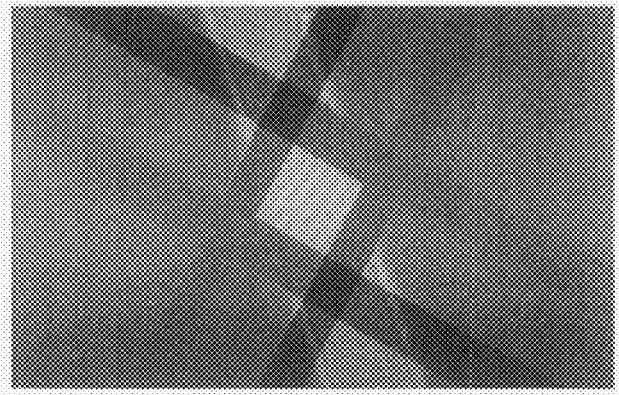
Figure 7D:
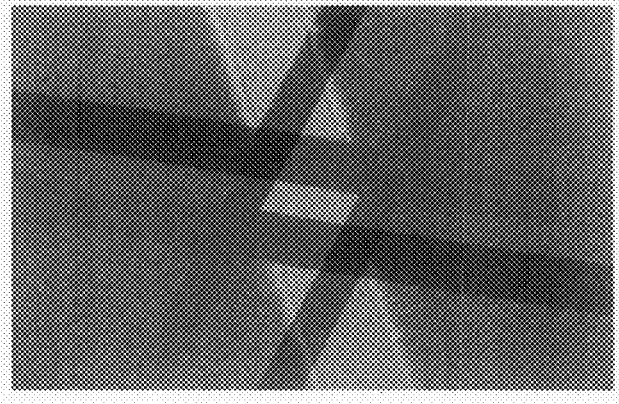
Figure 8A:
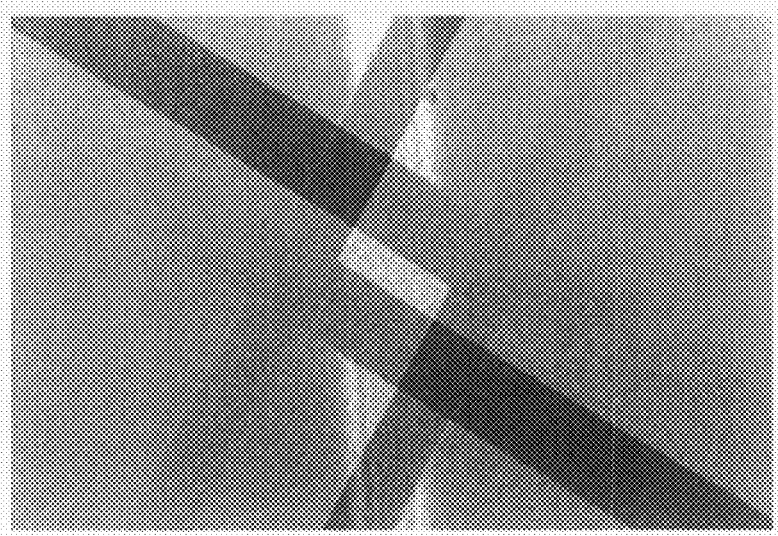
FIGS. 8(A) to 8(C) are experimental results obtained by fixing the filament electrode $9_1$ of the upper-stage electron biprism and the filament electrode $9_2$ of the intermediate-stage electron biprism in the state of that they are orthogonal to each other ($\Phi_1=90°$), by changing the azimuth angle $\Phi_3$ formed by the filament electrode $9_2$ of the intermediate-stage electron biprism and the filament electrode $9_3$ of the lower-stage electron biprism, and experimental results observed the shape change of an interference area.
Figure 8B:
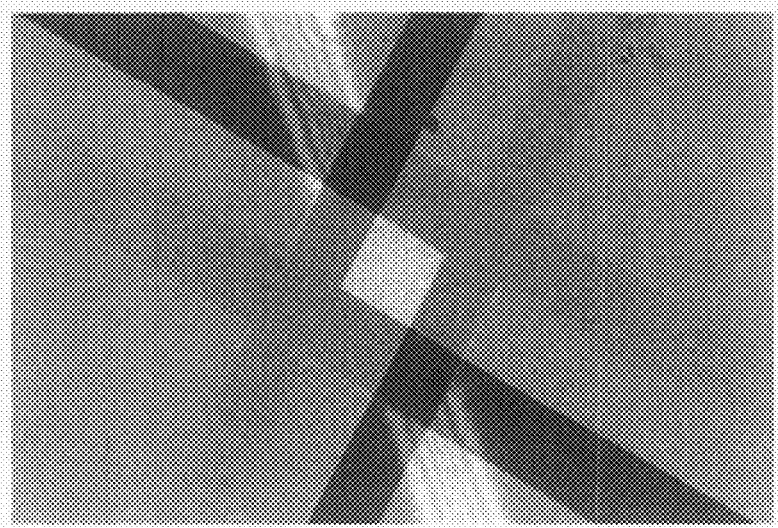
Figure 8C:
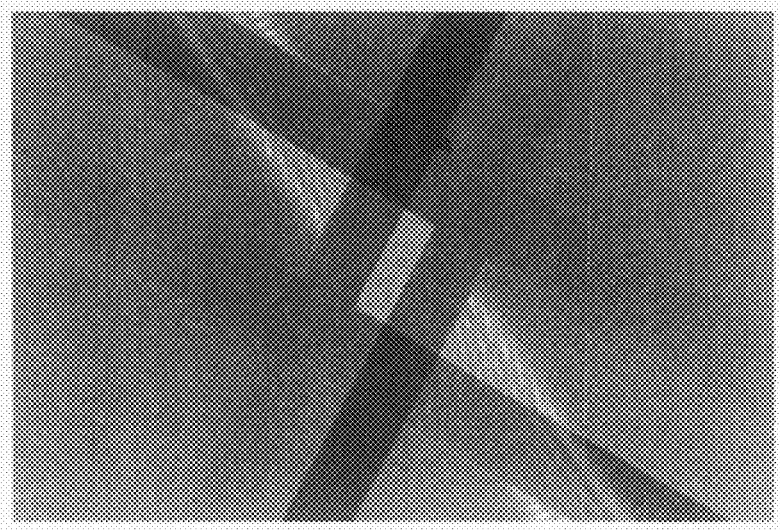
Figure 9A:
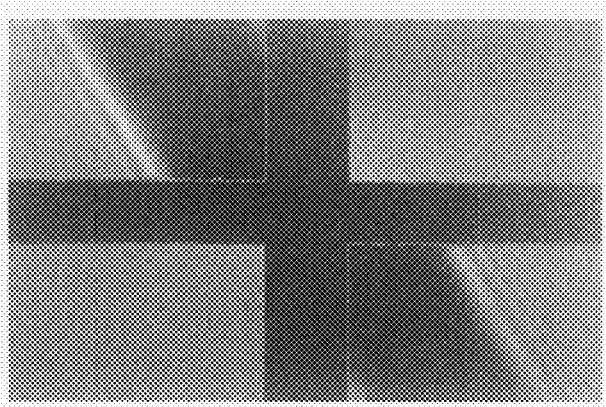
FIGS. 9(A) to 9(D) are experimental results showing the variation of the shape of an interference area by an applied voltage $V_3$ on the filament electrode of the lower-stage electron biprism when the azimuth angles among the filament electrodes of the electron biprisms are constant.
Figure 9B:
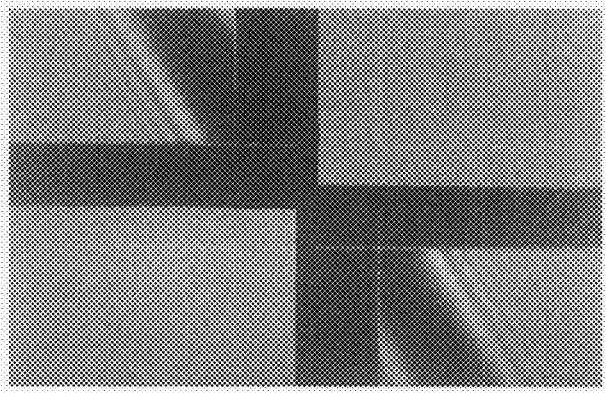
Figure 9C:
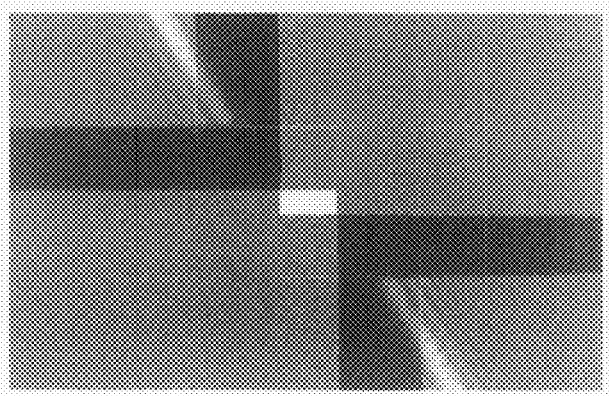
Figure 9D:
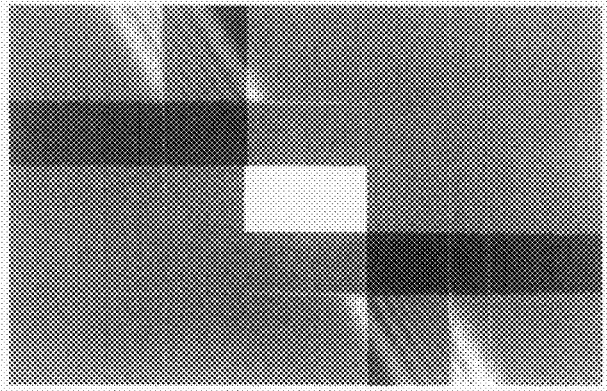
Figure 10:
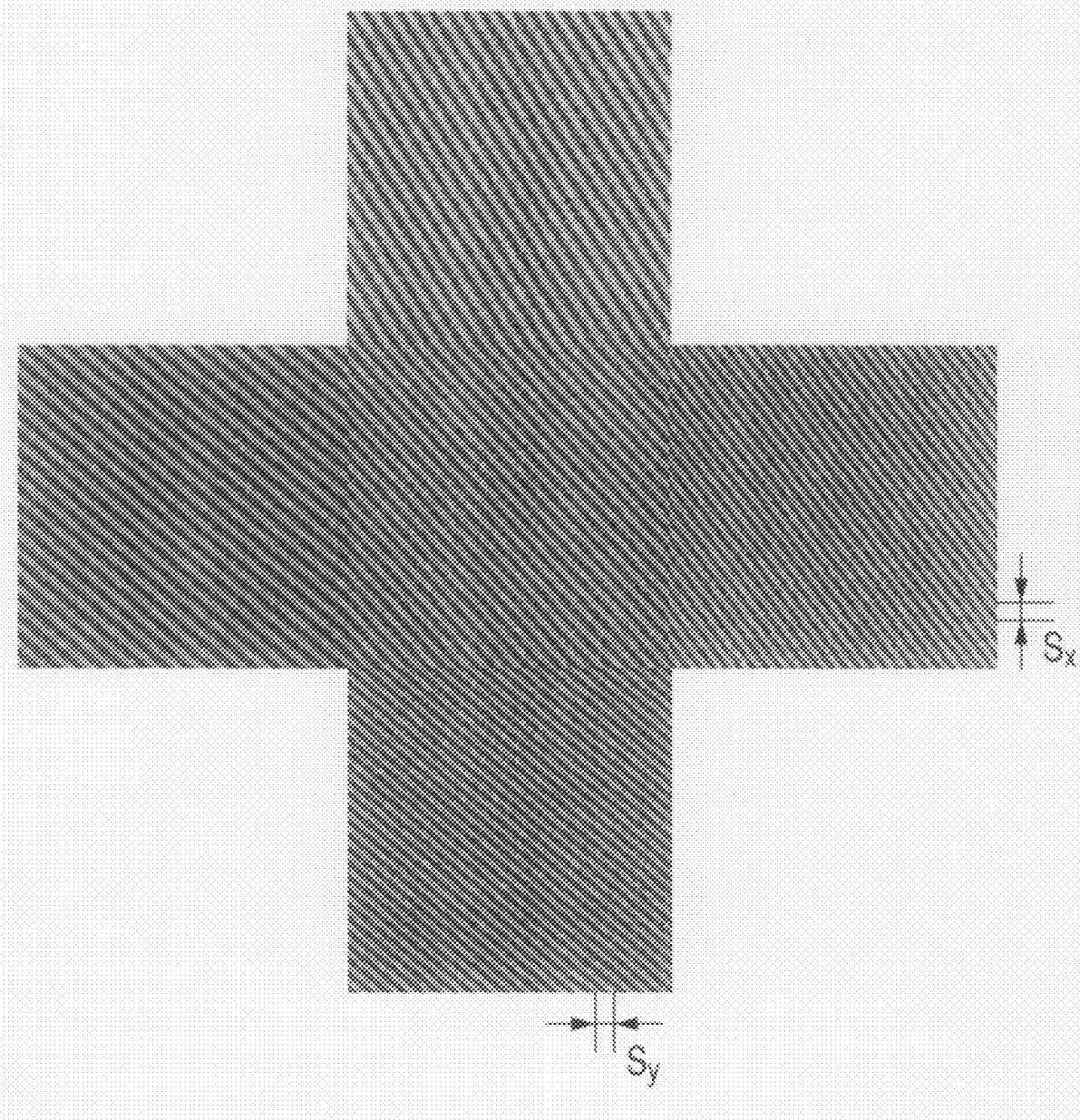
FIG. 10 are experimental results showing the variation of the interference fringe spacing ($s_x$, $s_y$) in the X-axis and Y-axis directions in which to clearly observe the interference fringe spacing s and the azimuth θ in the interferogram, the center portion in the interference area shown in FIG. 9(D) is extracted and enlarged.
Figure 11A:
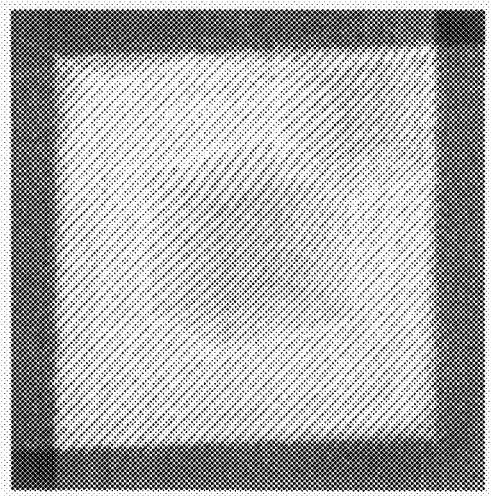
FIGS. 11(A) to 11(C) are examples of the electron holograms obtained by controlling an applied voltage $V_1$ to the upper-stage biprism and an applied voltage $V_2$ to the intermediate-stage biprism, and changing the interference fringe spacing s in the state that the azimuth θ of the interference fringes is maintained constant (θ=−45°)
Figure 11B:
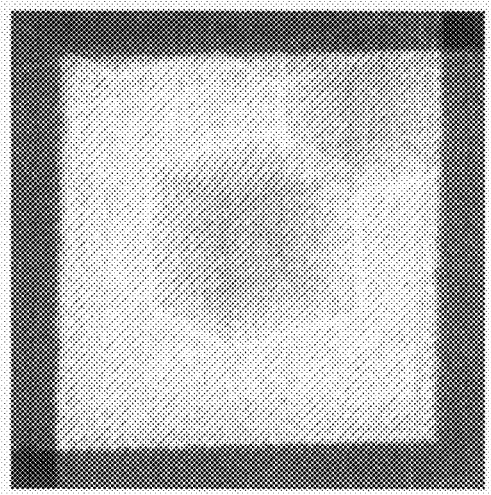
Figure 11C:
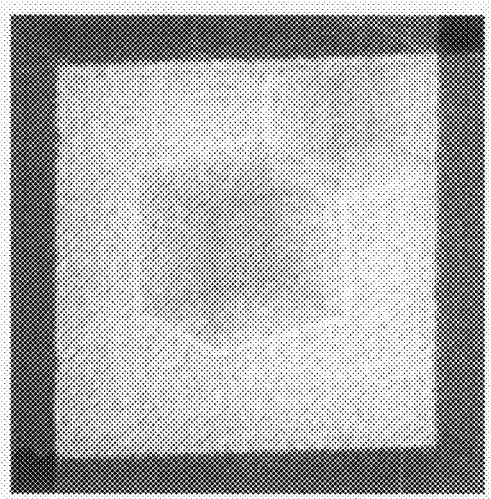
Figure 12A:
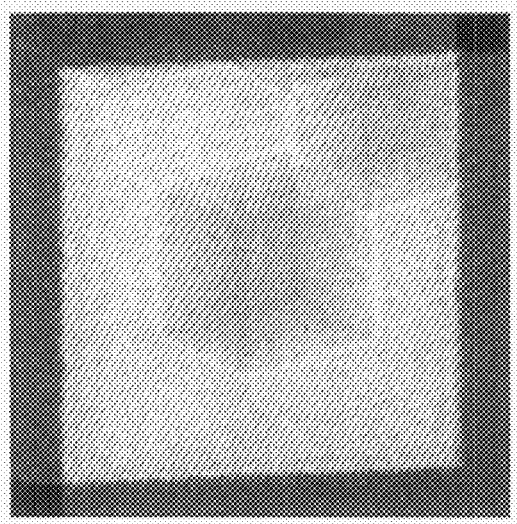
FIGS. 12(A) to 12(C) are examples of the electron holograms obtained by controlling the applied voltage $V_1$ to the upper-stage electron biprism and the applied voltage $V_2$ to the intermediate-stage electron biprism, and changing only the azimuth θ of the interference fringes in the state that the interference fringe spacing s is maintained constant ($S_{Obj}$=4 nm)
Figure 12B:
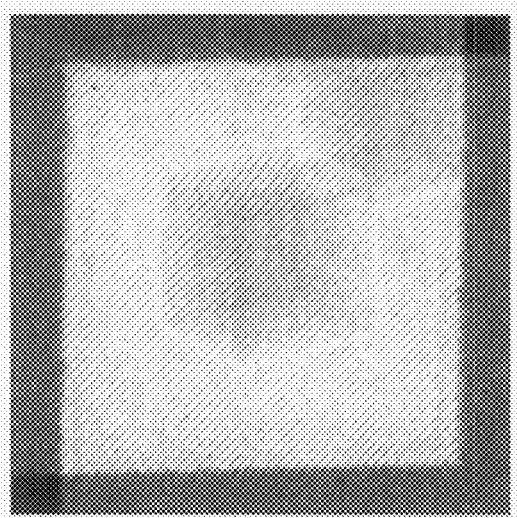
Figure 12C:
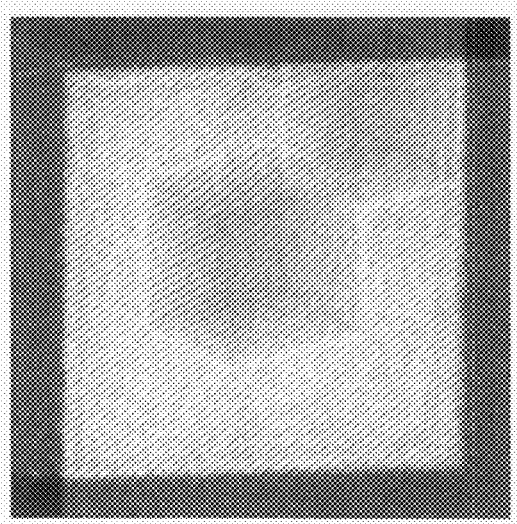
Figure 13:
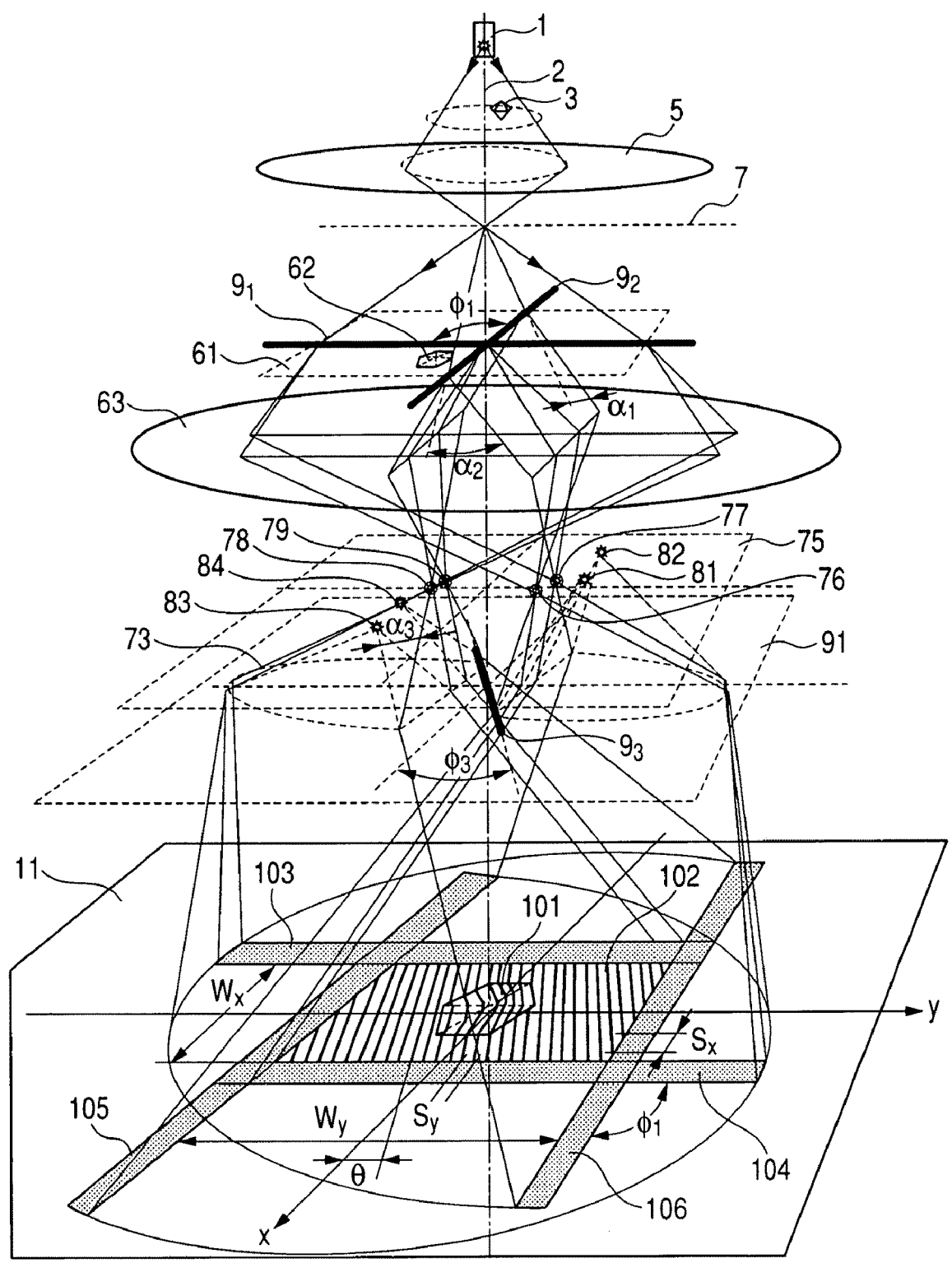
FIG. 13 is a schematic diagram showing an optical system in which two filament electrodes corresponding to a filament electrode $9_1$ of the upper-stage biprism and a filament electrode $9_2$ of the intermediate-stage electron biprism of the triple-biprism electron interferometer explained in Embodiment 1 are orthogonal to each other to be mounted on the plane 61 of the upper-stage electron biprism and a filament electrode $9_3$ of the lower-stage electron biprism is mounted on a plane 91.
Figure 14:
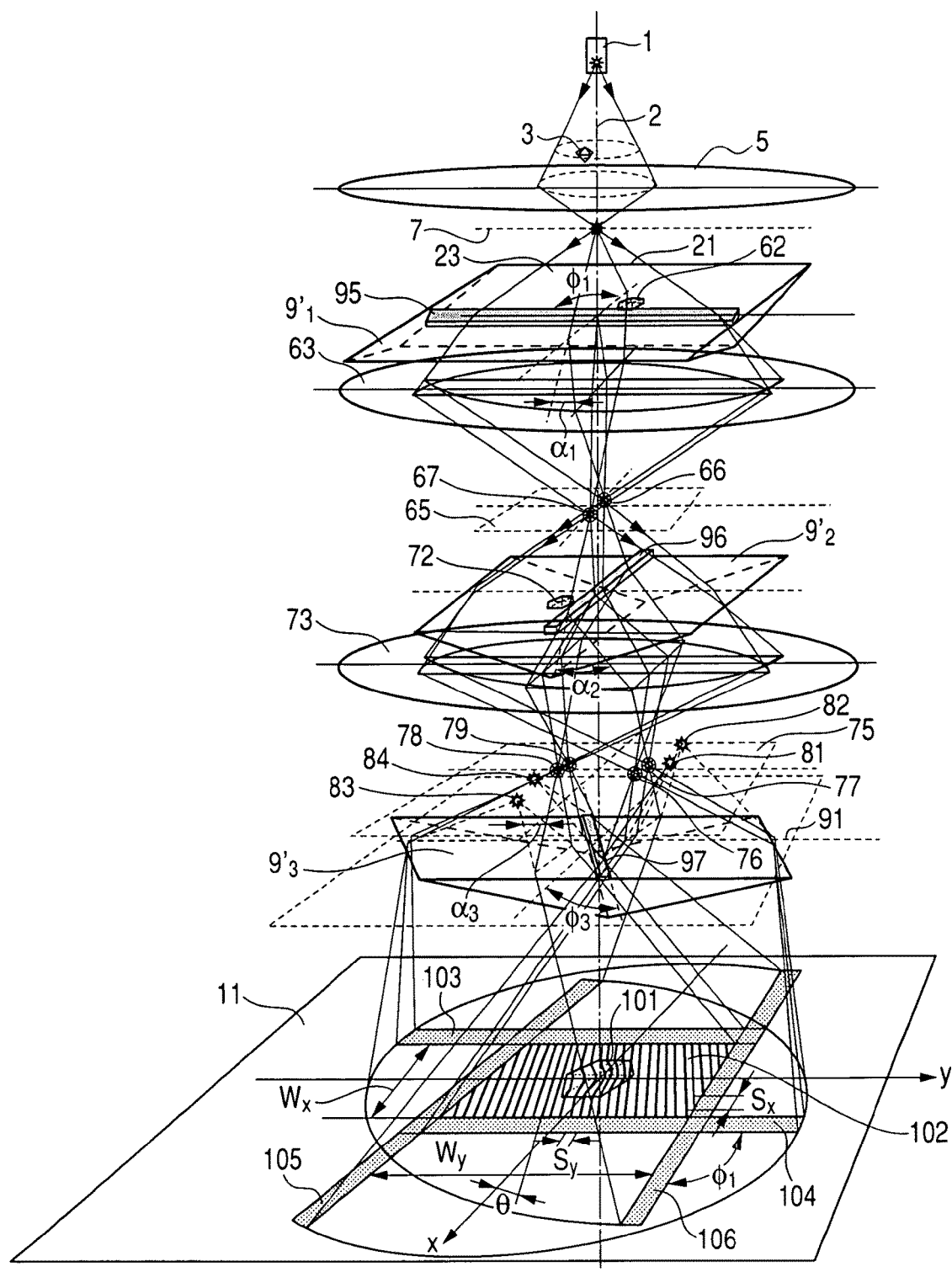
FIG. 14 is a schematic diagram showing an example in which three optical biprisms are arranged in place of the electron biprisms $9_1$, $9_2$, and $9_3$ of the optical system shown in FIG. 4 and beam stoppers for intercepting light beam are provided in the respective center positions (the back side of the ridge line positions) of the upper-stage, intermediate-stage, and lower-stage optical biprisms.
Figure 15:
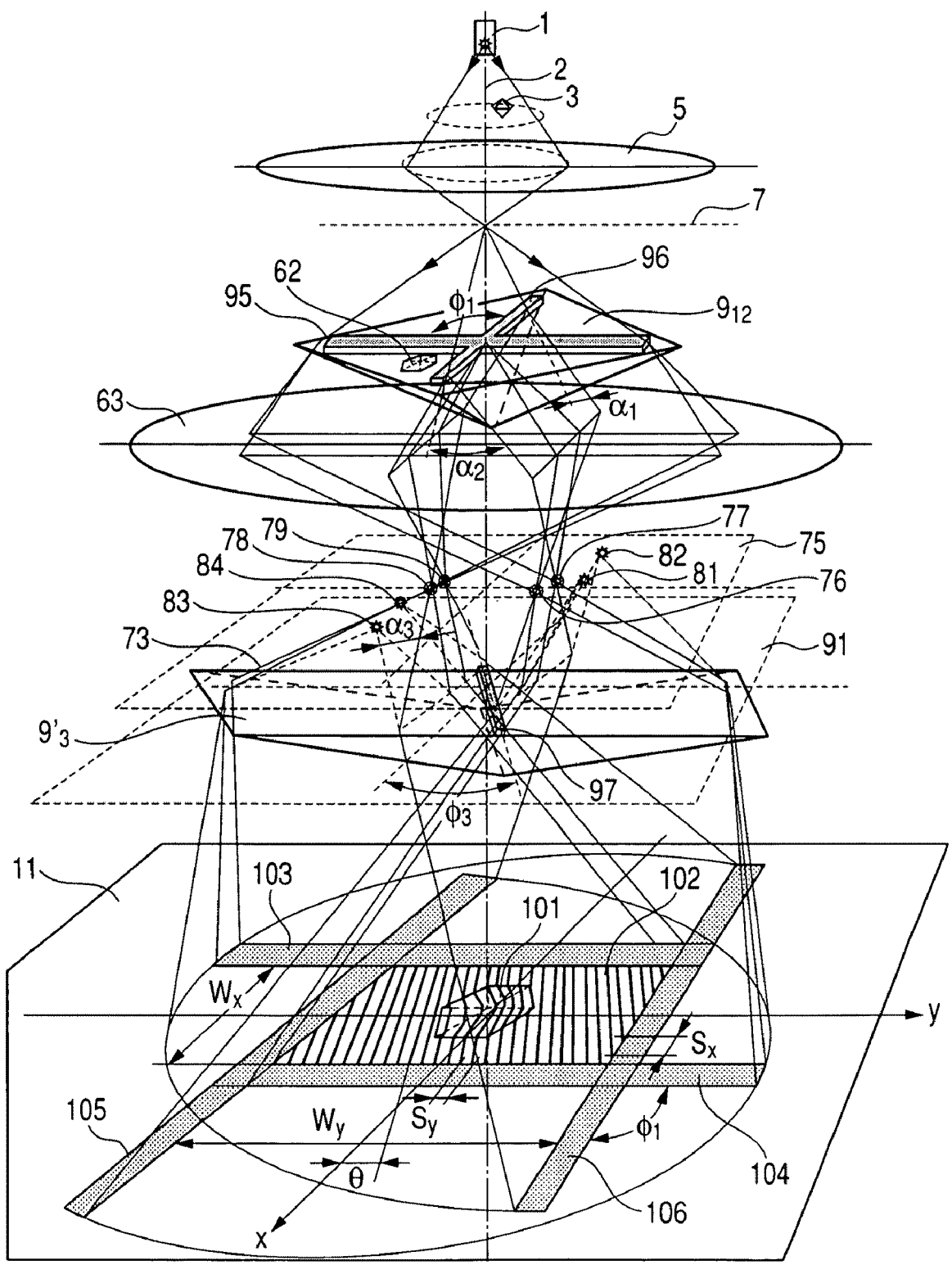
FIG. 15 is a schematic diagram showing the optical system for realizing the present invention to the optical interferometer using light beam according to the filament electrodes in one plane shown in FIG. 13.

1 . . . electron source, 2 . . . optical axis, 3 . . . specimen, 5 . . . objective lens system, 7 . . . first image plane of electron source, $9_1$ . . . filament electrode of an upper-stage electron biprism, $9_2$ . . . filament electrode of an intermediate-stage electron biprism, $9_3$ . . . filament electrode of a lower-stage electron biprism, 11 . . . observation plane, 21 . . . object wave, 23 . . . reference wave, 61 . . . first image plane, 62 . . . specimen image on the first image plane 61, 63 . . . first magnifying lens system, 65 . . . second image plane of electron source, 66, 67 . . . real images of the electron source on the second electron-source image plane 65, 71 . . . second image plane, 72 . . . specimen image on the second image plane 71, 73 . . . second magnifying lens system, 75 . . . third image plane of electron source, 76 to 79 . . . real images of the electron source on the third electron-source image plane 75, 81 to 84 . . . virtual image of the electron source on the third electron-source image plane 75, 91 . . . plane on which the filament electrode of the lower-stage electron biprism is located, 92 . . . third image plane, 101 . . . specimen image on the observation plane 11, 103 to 106 . . . shades of the filament electrodes of the upper-stage and intermediate-stage electron biprisms on the observation plane 11, $9'_1$ . . . optical biprism in place of the electrode of the upper-stage electron biprism, $9'_2$ . . . optical prism in place of the electrode of the intermediate-stage electron biprism, $9'_3$ . . . optical prism in place of the electrode of the lower-stage electron biprism, $9_{12}$ . . . optical prism in place of the electrodes of the upper-stage and intermediate-stage electron biprisms, 95 to 97 . . . beam stoppers for light beam

The invention claimed is:

1. A charged particle beam apparatus comprising: a source of a charged particle beam; a condenser optical system for irradiating a specimen with the charged particle beam emitted from the source; a specimen holder for holding the specimen irradiated with the charged particle beam; an imaging lens system for imaging the specimen; a device for observing or recording the specimen image; an objective lens system formed by one lens or a plurality of lenses capable of controlling focal lengths independently in the imaging lens system positioned on the downstream side on the traveling direction of the charged particle beam from the specimen position on an optical axis of the charged particle beam; an upper-stage biprism located in a plane orthogonal to the optical axis at a position of an image plane of the specimen determined by the objective lens system on the downstream side of the objective lens system; an intermediate-stage biprism located in a plane in parallel with the plane where the upper-stage biprism is placed formed on the downstream side of the upper-stage biprism through one or more lenses in the imaging lens system; and a lower-stage biprism located in a plane in parallel with the plane where the upper-stage biprism is placed on the downstream side of the intermediate-stage biprism through one or more lenses in the imaging lens system, the three biprisms being capable of moving of their positions and rotating of their azimuth in the respective plane independently, wherein voltages can be applied to the upper-stage biprism, the intermediate-stage biprism, and the lower-stage biprism independently to deflect the charged particle beam in an arbitrary direction, and wherein in a case that an azimuth angle between the intermediate-stage biprism and the upper-stage biprism is $\Phi_1$, and an azimuth angle between the intermediate-stage briprism and the lower-stage biprism is $\Phi_3$, the charged particle beam is deflected in a condition that $\Phi_3$ is not zero and $\Phi_3$ is not $\Phi_1$.

2. The charged particle beam apparatus according to claim 1, wherein the specimen image formed in an arbitrary magnification in a plane where the upper-stage biprism is positioned with orthogonal to the optical axis, by adjusting the focal lengths of the respective lenses of the objective lens system having the plurality of lenses.

3. The charged particle beam apparatus according to claim 1, wherein the lower-stage biprism is positioned on the downstream side of a lens placed on the downstream side of the intermediate-stage biprism on the optical axis of the charged particle beam, and is positioned on the downstream side of an image of the source formed by the lens.

4. The charged particle beam apparatus according to claim 1, wherein the lower-stage biprism is positioned on the downstream side of a lens placed on the downstream side of the intermediate-stage biprism on the optical axis of the charged particle beam, and is positioned between the lens and an image of the source formed by the lens.

5. A charged particle beam apparatus comprising: a source of a charged particle beam; a condenser optical system for irradiating a specimen with the charged particle beam emitted from the source; a specimen holder for holding the specimen irradiated with the charged particle beam; an imaging lens system for imaging the specimen; a device for observing or recording the specimen image; an objective lens system formed by one lens or a plurality of lenses capable of controlling focal lengths independently in the imaging lens system positioned on the downstream side on the traveling direction of the charged particle beam from the specimen position on an optical axis of the charged particle beam; an upper-stage quadrangular-pyramid prism located in a plane orthogonal to the optical axis at a position of an image plane of the specimen determined by the objective lens system on the downstream side of the objective lens system; and a lower-stage biprism located in a plane in parallel with the plane where the upper-stage quadrangular-pyramid prism is placed on the downstream side of the upper-stage quadrangular-pyramid prism through one or more lenses in the imaging lens system, the two prisms being capable of moving of the positions and rotating of their azimuth in the respective plane independently, wherein voltages can be applied to the upper-stage quadrangular-pyramid prism and the lower-stage biprism independently to deflect the charged particle beam in an arbitrary direction.

6. The charged particle beam apparatus according to claim 5, wherein the specimen image formed in an arbitrary magnification in a plane where the upper quadrangular-pyramid prism is positioned with orthogonal to the optical axis by adjusting the focal lengths of the respective lenses of the objective lens system having the plurality of lenses.

7. The charged particle beam apparatus according to claim 5, wherein the lower-stage biprism is positioned on the downstream side of a lens placed on the downstream side of the upper-stage quadrangular-pyramid prism on the optical axis of the charged particle beam, and is positioned on the downstream side of an image of the source formed by the lens.

8. The charged particle beam apparatus according to claim 5, wherein the lower-stage biprism is positioned on the downstream side of a lens placed on the downstream side of the upper-stage quadrangular-pyramid prism on the optical axis of the charged particle beam, and is positioned between the lens and an image of the source formed by the lens.

9. The charged particle beam apparatus according to claim 5, wherein the deflection direction of the charged particle beam by the quadrangular-pyramid prism can be controlled by adjusting an azimuth angle formed between filament electrodes of two electron biprisms in the same image plane constituting the quadrangular-pyramid prism.

10. The charged particle beam apparatus according to claim 5, wherein the deflection angle of the charged particle beam by the quadrangular-pyramid prism can be controlled independently in the vertical direction with respect to the filament electrodes by adjusting applied voltages to filament electrodes of two electron biprisms in the same image plane constituting the quadrangular-pyramid prism.

* * * * *